US008509909B2

(12) United States Patent
Figueiredo et al.

(10) Patent No.: US 8,509,909 B2
(45) Date of Patent: Aug. 13, 2013

(54) USING TELEMETRY COUPLING AS A SURROGATE FOR RECHARGER COUPLING

(75) Inventors: Giselle Suraya Figueiredo, Minneapolis, MN (US); John W. Forsberg, St. Paul, MN (US); Jeffrey T. Keacher, Stanford, CA (US); Alex C. Toy, St. Paul, MN (US); Erik G. Widman, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1525 days.

(21) Appl. No.: 12/100,875

(22) Filed: Apr. 10, 2008

(65) Prior Publication Data
US 2009/0259273 A1     Oct. 15, 2009

(51) Int. Cl.
*A61N 1/372* (2006.01)
*A61N 1/378* (2006.01)

(52) U.S. Cl.
CPC .......... *A61N 1/37252* (2013.01); *A61N 1/3787* (2013.01)
USPC ............................. 607/60; 607/61

(58) Field of Classification Search
USPC ................. 607/30–34, 59–61; 128/903–904, 128/897–899
See application file for complete search history.

(56) References Cited

U.S. PATENT DOCUMENTS

| | | | |
|---|---|---|---|
| 3,942,535 A * | 3/1976 | Schulman | 607/33 |
| 5,758,667 A | 6/1998 | Slettenmark | |
| 5,948,006 A | 9/1999 | Mann | |
| 6,305,381 B1 | 10/2001 | Weijand et al. | |
| 6,516,227 B1 | 2/2003 | Meadows et al. | |
| 6,752,155 B2 | 6/2004 | Behm | |
| 2005/0075693 A1 | 4/2005 | Toy et al. | |
| 2006/0016452 A1 | 1/2006 | Goetz et al. | |
| 2008/0172109 A1* | 7/2008 | Rahman et al. | 607/60 |

FOREIGN PATENT DOCUMENTS

WO     WO98/11942     3/1998

OTHER PUBLICATIONS

PCT International Search Report and Written Opinion dated Apr. 14, 2009.

* cited by examiner

*Primary Examiner* — Carl H Layno
*Assistant Examiner* — Jessica Sarcione
(74) *Attorney, Agent, or Firm* — Beth L. McMahon

(57) ABSTRACT

Telemetry signal strength is used for positioning a primary recharge coil of a recharging unit at a location proximate to an Implantable Medical Device (IMD) in preparation to recharge a rechargeable power source of the IMD. An antenna of the recharging unit is positioned proximate to the IMD, a telemetry session is initiated between the two devices, and a value indicative of the telemetry signal strength is obtained. Using a known correspondence between telemetry signal strength and recharge coupling efficiency for the IMD/recharging unit pair, the telemetry signal strength value is used to determine whether adequate recharge coupling may be achieved between the pair of devices. If so, a recharge session may be established. Otherwise, the antenna is repositioned and the process is repeated. The correspondence between telemetry signal strength and recharge coupling efficiency for the device pair may be developed empirically or using modeling.

37 Claims, 13 Drawing Sheets

| Telemetry Signal Strength | Recharge Coupling Efficiency |
|---|---|
| 10 | 0% |
| 31 | 0% |
| 47 | 10% |
| 100 | 50% |
| 128 | 70% |
| 140 | 75% |
| 200 | 80% |
| 221 | 86% |

Signal Strength Map

| Telemetry Signal Strength | Recharge Coupling Efficiency |
|---|---|
| 10 | 0% |
| 31 | 0% |
| 47 | 10% |
| 100 | 50% |
| 128 | 70% |
| 140 | 75% |
| 200 | 80% |
| 221 | 86% |

Signal Strength Map

FIG. 5

Reposition Antenna:

10% / 70% / 86% current   min    max

FIG. 9A

Recharging:

70% / 80% / 86% min   current   max

FIG. 9B

USING TELEMETRY COUPLING AS A SURROGATE FOR RECHARGER COUPLING

FIELD OF THE INVENTION

This invention relates to IMDs and, in particular, to energy transfer devices, systems and methods for IMDs.

BACKGROUND OF THE INVENTION

Implantable Medical Devices (IMDs) for producing a therapeutic result in a patient are well known. For example, implantable neurostimulators are available for the treatment of pain, movement disorders such as Parkinson's disease, essential tremor, dystonia, gastric disorders, incontinence, sexual disfunction, migraine headaches, and other conditions. Other examples of IMDs include, but are not limited to, implantable drug infusion pumps, cardioverters, cardiac pacemakers, defibrillators, and cochlear implants.

All of the foregoing types of IMDs require electrical power to perform their therapeutic function, which may include driving an electrical infusion pump, providing an electrical neurostimulation pulse, or providing an electrical cardiac stimulation pulse. This electrical power is derived from a power source.

Typically, a power source for an IMD can take one of two forms. The first form utilizes an external power source that transcutaneously delivers energy via wires or radio frequency energy. However, having electrical wires that perforate the skin is disadvantageous due, in part, to the risk of infection. Further, continuously coupling patients to an external power source for therapy is a large inconvenience.

The second type of power source utilizes single cell batteries to provide energy to the IMD. This can be effective for low-power applications such as pacing devices. However, such single cell batteries usually do not supply the lasting power required to perform therapies provided by newer IMDs. In some cases, such as an implantable artificial heart, a single cell battery might last the patient only a few hours. In other, less extreme cases, a single cell unit might expel all or nearly all of its energy in less than a year. This will necessitate the explant and re-implant of the IMD.

One mechanism that addresses the foregoing limitations allows electrical power to be transcutaneously transferred through the use of inductive coupling. The transferred electrical power can optionally be stored in a rechargeable battery. This battery can then be used to provide direct electrical power to the IMD. When the battery has expended, or nearly expended, its capacity, the battery can be recharged transcutaneously.

Transcutaneous energy transfer through the use of inductive coupling involves the placement of two coils positioned in close proximity to each other on opposite sides of the skin (i.e., cutaneous boundary). One of these coils is external to the patient, and is placed against the patient's skin in the vicinity of the IMD. This external, or primary, coil is associated with an external power source or external charger or recharger. A secondary coil is implanted within the patient, and may be part of the IMD or otherwise associated therewith.

In one embodiment, the primary coil is driven by the external power source with an alternating current. This induces a current in the secondary coil through inductive coupling. This induced current may be used to power the IMD and/or to charge or recharge an internal power source.

For IMDs, the efficiency at which energy is transcutaneously transferred may be crucial for several reasons. First, the inductive coupling has a tendency to heat surrounding components and tissue. Since it is desirable to limit this heating effect, the amount of energy transfer per unit time must also be limited. The higher the efficiency of energy transfer, the more energy that can be transferred while at the same time limiting the heating of surrounding tissue.

In addition to the foregoing, it is desirable to limit the amount of time required to achieve a desired charge, or recharge, of an internal power source. While charging or recharging is occurring, the patient necessarily has an external encumbrance attached to his or her body. This attachment may impair the patient's mobility and limit the patient's comfort. The higher the efficiency of the energy transfer system, the faster the desired charging or recharging can be completed, thus limiting inconvenience to the patient.

Finally, the amount of energy available to the IMD may be limited by the amount of time the patient is willing to devote to recharging the device. The higher the efficiency of the energy transfer system, the greater the amount of energy that can be transferred during the recharge time. This increases the practical size of the internal power source, and allows for use of IMDs having higher power use requirements. This may also extend the time between charging.

One way to increase the efficiency of energy transfer is to position the primary coil optimally with respect to the secondary coil. Some existing implantable medical device systems incorporate a locating feature to locate, and align, the secondary coil with respect to the primary coil. This feature has variously been implemented using a metal detection approach that involves measuring the loading of the external antenna caused by the proximity of the implant. When the loading is at a maximum, a high-efficiency coupling has been achieved. However, because the loading of the system is affected by non-device metallic objects in the vicinity of the device, false results can be produced, resulting in non-optimal alignment.

Other solutions use power measurements in the IMD to determine the efficiency of the energy transfer. In such systems, a recharge session is initiated. After the recharge session begins, one or more sensors in the IMD measure current in, and/or voltage across, the secondary coil. Periodically, the recharge session is temporarily halted so that the IMD may transfer the measurements to the recharging unit. These measurements may then be used to determine the efficiency of the energy transfer. For instance, the power associated with the primary coil may be compared to that measured in the secondary coil to determine the efficiency of the power transfer. If the efficiency is not adequate, the position of the primary coil may be moved with respect to the IMD and the process is repeated.

As a variation of the foregoing, current associated with the secondary coil may be measured. If the current induced in the secondary coil is above some minimum required current, the coupling efficiency is considered adequate. Otherwise, the primary coil must be repositioned and the process repeated.

The foregoing mechanisms of measuring electrical characteristics of a secondary coil during recharge do not occur in real time. A patient or clinician must position the primary coil at some location relative to the IMD and initiates a recharge session. Sometime thereafter, this recharge session is interrupted so that measurements taken during recharge may be transferred from the IMD to the recharging unit. One or more calculations to determine coupling efficiency may be performed and the results are communicated to the patient. If the efficiency is not adequate, the primary coil is repositioned, recharge is re-initiated, and the process is repeated. A single iteration may take a better part of a minute. Thus, finding the optimal location may take a substantial amount of time.

SUMMARY OF THE INVENTION

The invention is directed to techniques for using telemetry signal strength to position a primary recharge coil of a recharging unit at a location relative to a secondary recharge coil of an IMD so that a high-efficiency recharge session may be initiated. According to one embodiment, an antenna of the recharging unit is positioned in proximity to the IMD. This antenna may include both a primary recharging coil and a telemetry coil. A telemetry session is established between the IMD and the recharging unit. One or more telemetry signal strength measurements are obtained describing strength of an uplink and/or a downlink transmission of the telemetry session.

Next, the one or more telemetry signal strength measurements may be employed to obtain an indication of overall signal strength of the telemetry transmission between the IMD and the recharging unit when the antenna is at the current position. This indication of signal strength is then used to reference a signal strength map.

A signal strength map may be a table or another data structure that provides a correlation between telemetry signal strengths and recharge coupling efficiency for a given IMD/recharging unit device pair. Recharge coupling efficiency refers to the strength of the coupling that may be achieved between the secondary coil of the IMD and the primary coil of the recharging unit. The recharge coupling efficiency provides a reflection of how efficiently the recharge operation would occur if a recharge session were initiated with the recharging unit (and in particular, the antenna of the recharging unit) at the current location.

The indication of telemetry signal strength is used to reference the signal strength map, and to retrieve an associated value indicative of recharge coupling efficiency. If this indication of recharge coupling efficiency is considered inadequate, the user is prompted to reposition the antenna and the process may be repeated. Otherwise, a recharge session may be initiated.

In an alternative embodiment, the indication of telemetry signal strength need not be used to retrieve a corresponding recharge coupling efficiency value from the signal strength map. Instead, a determination is simply made as to whether the indication of signal strength has met some predetermined signal strength threshold value. If so, it is known that the recharge coupling efficiency is adequate with the antenna at the current position, and a recharge session may be initiated. Otherwise, the antenna must be repositioned and the process repeated.

A telemetry signal strength map for use with the current invention may be created in several ways. According to a first approach, it may be created empirically. During this empirical process, the antenna of the recharging unit is systematically positioned at various locations relative to the IMD while telemetry signal strength measurements and corresponding recharging coupling measurements are obtained. This information may then be stored as a data set within the signal strength map. This process may occur prior to implant or after implant of the IMD. In another embodiment, the process of collecting and associating telemetry signal strength measurements with recharging coupling efficiency measurements may be repeated at regular intervals. For instance, new measurements may be taken every $N^{th}$ time the signal strength map is used, where N is programmable. This allows the signal strength map to be adaptive. That is, the signal strength map will be modified over time to take into account changes that occur in the circuitry of the IMD (e.g., as the battery ages) and/or within the patient's body.

In another embodiment, a signal strength map may be developed for a given IMD/recharging unit pair using models rather than using empirical methods. Such models take into account the electromagnetic properties of the IMD and/or recharging unit, and may also take into account depth and orientation of an IMD within the patient's body.

According to one embodiment of the invention, a recharging system is disclosed. The recharging system is provided for use in recharging an IMD having a secondary recharge coil, a rechargeable power source, and an internal telemetry coil. The recharging system includes an external telemetry coil to exchange a telemetry signal with the internal telemetry coil of the IMD. The telemetry signal may be exchanged during at least one of an uplink and a downlink telemetry transmission. This system further comprises a communication circuit coupled to receive, and to provide an indication of signal strength of, the exchanged telemetry signal, and a control circuit coupled to receive the indication of signal strength. Based on the indication of signal strength, it is determined whether recharge coupling efficiency is adequate to initiate a recharge session between the recharging system and the IMD. If so, the recharge session may be automatically established, or a user may initiate the session to recharge the rechargeable power source of the IMD. If a determination is made that the recharge session cannot be initiated, a user may be provided with an indication to reposition an antenna of the recharging unit.

Another embodiment relates to a method for utilizing a recharging unit to recharge a rechargeable power source of an IMD. According to this method, at least one telemetry signal is transmitted between the recharging unit and the IMD. An indication of signal strength of the at least one telemetry signal is determined. Based on the indication of signal strength, it is determined whether adequate recharge coupling efficiency exists to initiate a recharge session. A value indicative of the recharge coupling efficiency may be determined from the indication of signal strength. At least one of the indication of signal strength and the indication of recharge coupling efficiency may be provided to a user for informational purposes. If it is determined a recharge session may not be initiated, the user is, in one embodiment, prompted to reposition an antenna of the recharging unit.

According to one aspect, the determination as to whether a recharge session may be initiated may be based on a signal strength map. In one implementation, the signal strength map includes at least one of a signal strength threshold value and a predetermined relationship. It will be determined that a recharge session should be initiated if the indication of signal strength has the predetermined relationship to the signal strength threshold value.

Another embodiment involves a recharging unit for recharging a power source of an IMD. The recharging unit includes a digital storage device for storing programmed instructions to cause a control circuit of the recharging unit to perform a method that includes transmitting a telemetry signal between the antenna and the IMD, and obtaining an indication of signal strength of the telemetry signal. The method further includes determining, based on the indication of signal strength, whether to initiate a recharge session between the recharging unit and the IMD.

Other aspects and embodiments of the invention will become apparent to those skilled in the art from the following Figures and the accompanying description.

BRIEF DESCRIPTION OF THE DRAWINGS

FIG. 5 is table illustrating one embodiment of a signal strength map.

FIGS. 9A and 9B illustrate screen shots of feedback messages and data provided during repositioning of an antenna.

DETAILED DESCRIPTION OF THE INVENTION

Figure 1:
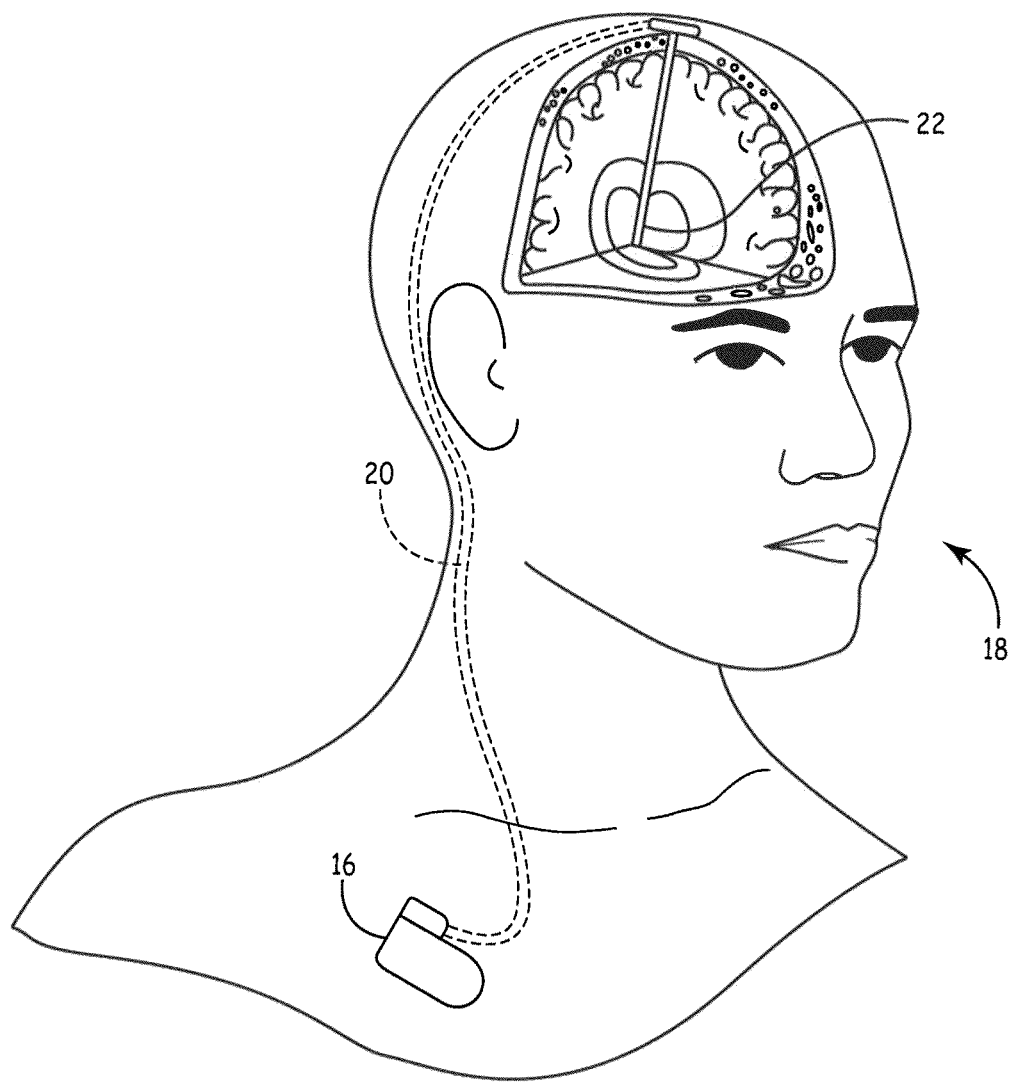
FIG. 1 is a diagram of an implantable medical device implanted in a patient.

FIG. 1 shows an exemplary IMD 16, which may be a neurostimulator, implanted in patient 18. IMD 16 can be any of a number of medical devices such as an implantable therapeutic substance delivery device, implantable drug pump, cardiac pacemaker, cardioverter or defibrillator, a device to delivery electrical stimulation pulses for a neurological or muscular condition or to alleviate pain, or any other IMD for delivering therapy.

The IMD 16 is typically implanted by a surgeon in a sterile surgical procedure performed under local, regional, or general anesthesia. One or more therapy connections 20 such as leads or catheters are typically implanted with a distal end positioned at a desired therapeutic delivery site 22. In the exemplary embodiment, a proximal end of a therapy connection 20 may be tunneled under the skin to the location where IMD 16 is to be implanted.

Figure 2:
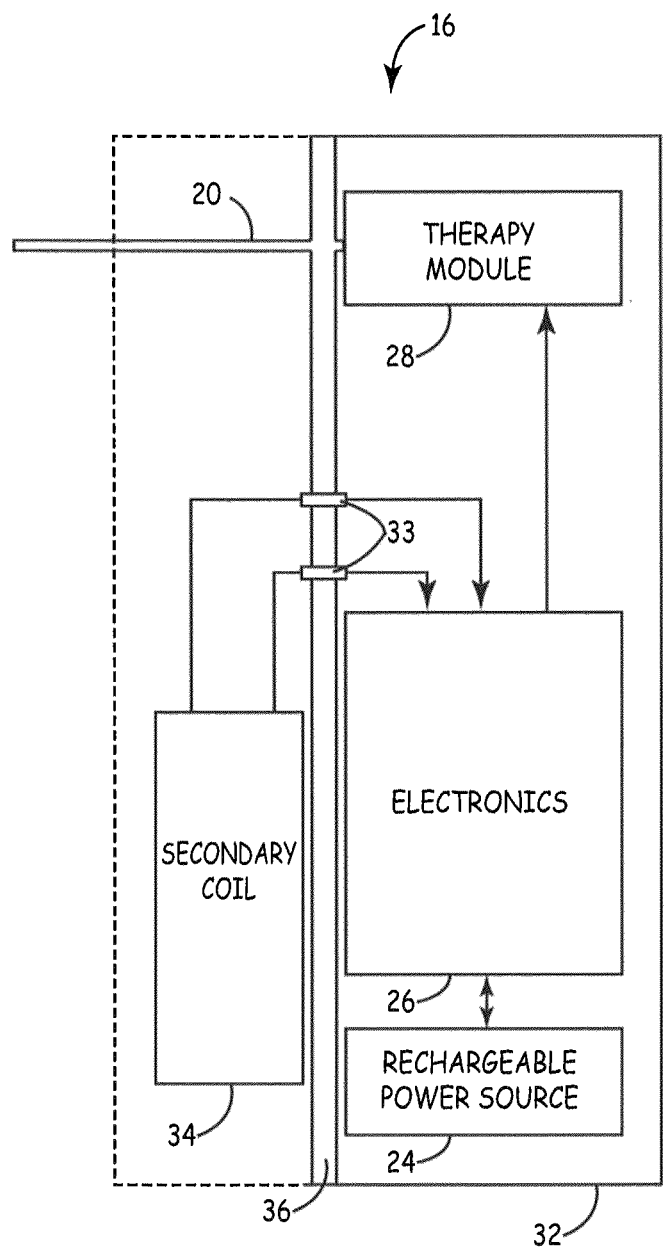
FIG. 2 is a block diagram of an exemplary implantable medical device that may utilize the current invention.

FIG. 2 is a block diagram of one embodiment of IMD 16. In FIG. 2, IMD 16 includes a rechargeable power source 24. Rechargeable power source 24 may be any of a variety of rechargeable power sources including a chemically-based battery or a capacitor. In one embodiment, rechargeable power source 24 is a lithium ion battery. Any other type of rechargeable battery suitable for powering an IMD may be used according to the current invention.

Rechargeable power source 24 is coupled to electronics 26, which includes circuitry to control the charging of rechargeable power source 24. Electronics 26 may include one or more microprocessors, application-specific integrated circuits (ASICs), digital signal processors (DSPs), field-programmable gate arrays (FPGAs), discrete electronic components, state machines, sensors, and/or other circuitry. One embodiment of electronics 26 is described further below in regards to FIG. 3.

Electronics 26 is, in turn, coupled, and provides power, to therapy module 28. Therapy module delivers some form of therapy to a patient. This therapy may include controlled delivery of a substance and/or electrical stimulation. For example, in one embodiment, therapy module 28 may include one or more output pulse generators such as capacitive elements, voltage regulators, current sources, and/or switches that are coupled to rechargeable power source 24 through electronics 26. Therapy module 28 may deliver electrical pulses to patient 18 via a combination of electrodes. Therapy module 28 is coupled to patient 18 through one or more therapy connections 20 such as leads or catheters.

Rechargeable power source 24, electronics 26 and therapy module 28 are generally contained in hermetically sealed housing 32. A secondary recharge coil ("secondary coil") 34 may be attached to the exterior of housing 32 and operatively coupled through electronics 26 to rechargeable power source 24. In an alternative embodiment, secondary coil 34 may be contained inside housing 32 or may instead be contained in a separate housing umbilically connected to electronics 26.

In one embodiment, a magnetic shield 36 may be positioned between secondary coil 34 and housing 32. In this embodiment, secondary coil 34 is coupled to electronics 26 via feedthroughs 33. The use of magnetic shield 36 protects rechargeable power source 24, electronics 26 and therapy module 28 from electromagnetic energy when secondary coil 34 is utilized to charge rechargeable power source 24 and also increases efficiency of energy transfer.

Figure 3:
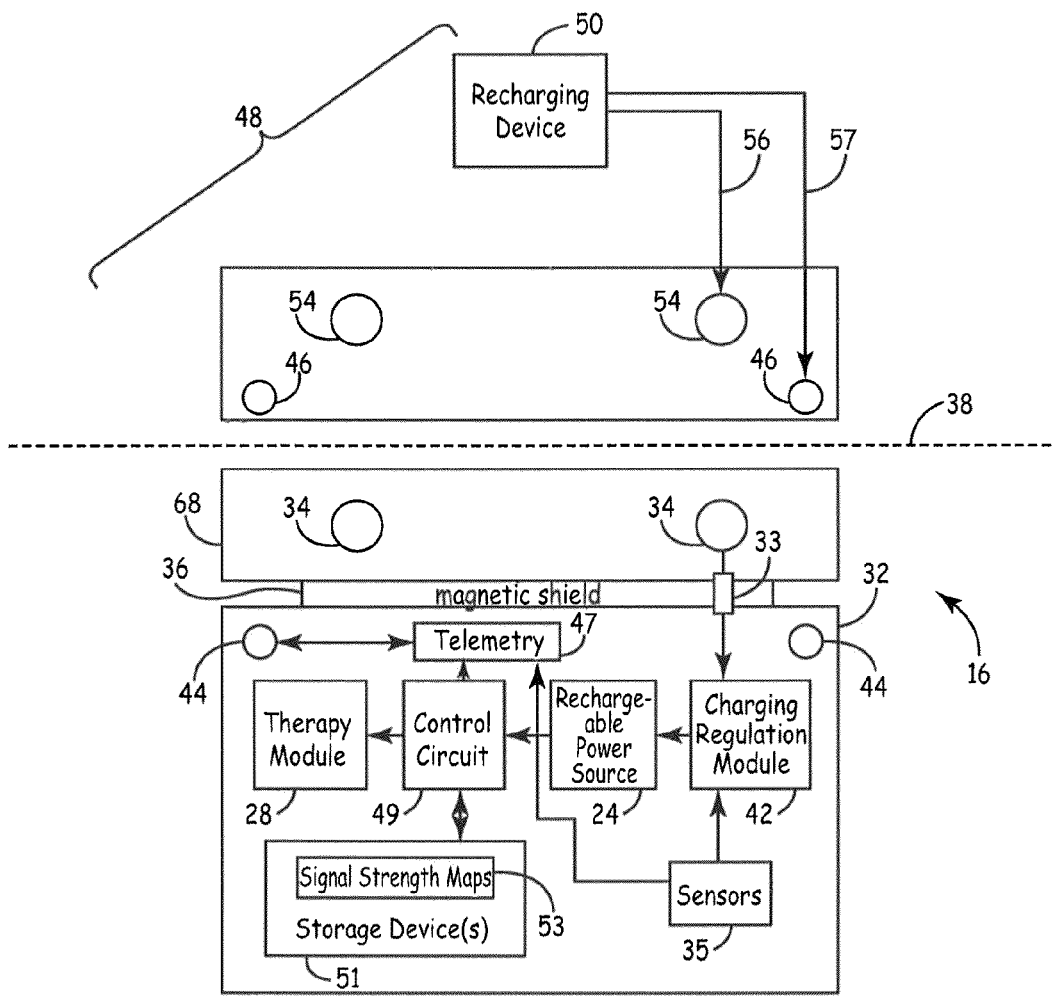
FIG. 3 is a more detailed block diagram of an implantable medical device situated under the cutaneous boundary with a recharging unit positioned on the other side of the cutaneous boundary.

FIG. 3 is a more detailed block diagram of IMD 16 situated under cutaneous boundary 38 and further illustrating a recharging unit 48 positioned on the other side of the cutaneous boundary. A cross-sectional view of secondary coil 34 and magnetic shield 36 is illustrated. Secondary coil 34 is coupled to a charging regulation module 42, which is provided to control a charging rate of rechargeable power source 24. One or more sensors 35 may be coupled to secondary coil 34 and/or charging regulation module 42 to measure current in, and/or voltage across, the secondary coil. These measurements may be used to determine how much power is being transferred to secondary coil 34, as will be discussed further below.

Charging regulation module 42 controls a charging rate of power source 24. This power source provides power to a control circuit 49, which may include a microprocessor, an ASIC, a DSP, discrete components, and/or any other type of circuitry. Control circuit 49 controls generation of therapy by therapy module 28.

Control circuit 49 is coupled to one or more storage device(s) 51. These storage devices may store software, firmware, and other types of programmed instructions for use in controlling operation of control circuit 49. According to the current invention, storage devices 51 may also store data structures and programmed parameters such a signal strength map(s) 53. Use of signal strength map(s) will be discussed further below in reference to the current invention.

Storage device(s) 51 may include volatile, non-volatile, magnetic, optical, and/or electrical media for storing digital data and programmed instructions, including random access memory (RAM), read-only memory (ROM), non-volatile RAM (NVRAM), electrically erasable programmable ROM (EEPROM), flash memory, removable storage devices, and the like.

Finally, IMD 16 is shown to include an internal telemetry coil 44 (illustrated in cross-section), which may be configured to communicate with an external device. Coil 44 is coupled to a communication circuit such as telemetry circuit 47 that is used to facilitate communication sessions with recharging unit 48 under the control of control circuit 49. This may be accomplished, for instance, using RF telemetry techniques performed according to the 802.11 or Bluetooth specification sets. Alternatively, infrared communication may be performed according to the IRDA specification set, or other standard or proprietary telemetry protocols may be used.

Telemetry coil 44 and secondary coil 34 may be of many different shapes and sizes. In one exemplary embodiment, telemetry coil 44 may be rectangular in shape with dimensions of 4.7 cm by 4.8 cm (1.85 inches by 1.89 inches) and constructed from 150 turns of 43 AWG wire. Secondary coil 34 may be constructed with 182 turns of 30 AWG wire with an inside diameter of 1.8 cm (0.72 inches), an outside diameter of 3.6 cm (1.43 inches), and a height of 0.2 cm (0.075 inches). Magnetic shield 36 is positioned between secondary coil 34 and housing 32 and sized to cover the footprint of secondary coil 34.

It will be understood that the coil configuration of the IMD discussed above is merely exemplary, and many other embodiments are possible. For instance, both coils 34 and 44 may be generally circular, both may be rectangular, one may be circular and the other rectangular, or either or both of the coils may be of a different shape. Either coil may be larger than the other, or the coils may be the same size. Moreover, coils 34 and 44 may, but need not be, co-axial such that the major axis of one coil is substantially aligned with the major axis of the other coil. Additionally, one or more of coils 34 and 44 may, but need not, be co-axial with a coil of external recharging unit 48, as will be discussed below.

External recharging unit 48 is provided to recharge rechargeable power source 24. External recharging unit 48 includes a recharging device 50 that is coupled via cables 56 and 57 to an external antenna 52 (shown in cross-section). In an alternative embodiment, recharging device 50 and antenna 52 may be combined into a single unit.

Antenna 52 includes a primary recharge coil 54 ("primary coil", shown in cross-section), which is coupled to recharging device 50 via cable 56. During a recharge session, recharging device 50 generates a current in recharge coil 54. When primary coil 54 is positioned proximate to secondary coil 34, the current in primary coil 54 inductively couples the primary coil to secondary coil 34. A resulting current in secondary coil 34 is employed to recharge rechargeable power source 24.

Antenna 52 further includes external telemetry coil 46. Telemetry coil 46, which is coupled to recharging device 50 via cable 57, is provided to allow recharging device 50 to communicate with IMD 16. For example, a communication session may be initiated via external telemetry coil 46 and telemetry coil 44 of IMD 16. During this communication session, information may be transferred from the recharging device 50 to the IMD in what is referred to as "downlink telemetry". The IMD may similarly transfer information from the IMD to the recharging device 50 during "uplink telemetry"

The strength of a signal between external telemetry coil 46 and internal telemetry coil 44 may be measured during downlink telemetry. Likewise, the strength of a signal between internal telemetry coil 44 and external telemetry coil 46 may be measured during uplink telemetry. Either, or both, of these measurements may be employed to generate a metric indicative of telemetry signal strength. According to the current invention, this signal strength metric may be employed to determine whether adequate recharge coupling may be achieved. This will be discussed in detail below.

Before continuing, it may be noted that in the current embodiment, IMD 16 includes magnetic shield 36, which absorbs electromagnetic energy. As a result, internal telemetry coil 44 of IMD 16 has been selected to have a larger diameter than secondary coil 34 so that the internal telemetry coil is not completely covered by magnetic shield 36. This allows a communication session to be established between external telemetry coil 46 and internal telemetry coil 44. Otherwise, the presence of magnetic shield 36 may interfere with signal transmission and prevent the communication link from being established. In an embodiment that omits magnetic shield 36, internal telemetry coil 44 need not be larger than secondary coil 34.

Recharging device 50 may drive primary coil 54 via batteries such that a patient may be somewhat ambulatory while charging IMD 16. In this embodiment, a desktop recharging system (not shown) which is coupled to an AC or DC power source may be coupled to recharging device 50 to periodically recharge the batteries of recharging device 50. In another embodiment, recharging device 50 may be coupled via a power cord to a source of AC power, such as a standard wall outlet when a recharge session is to be initiated.

Figure 4:
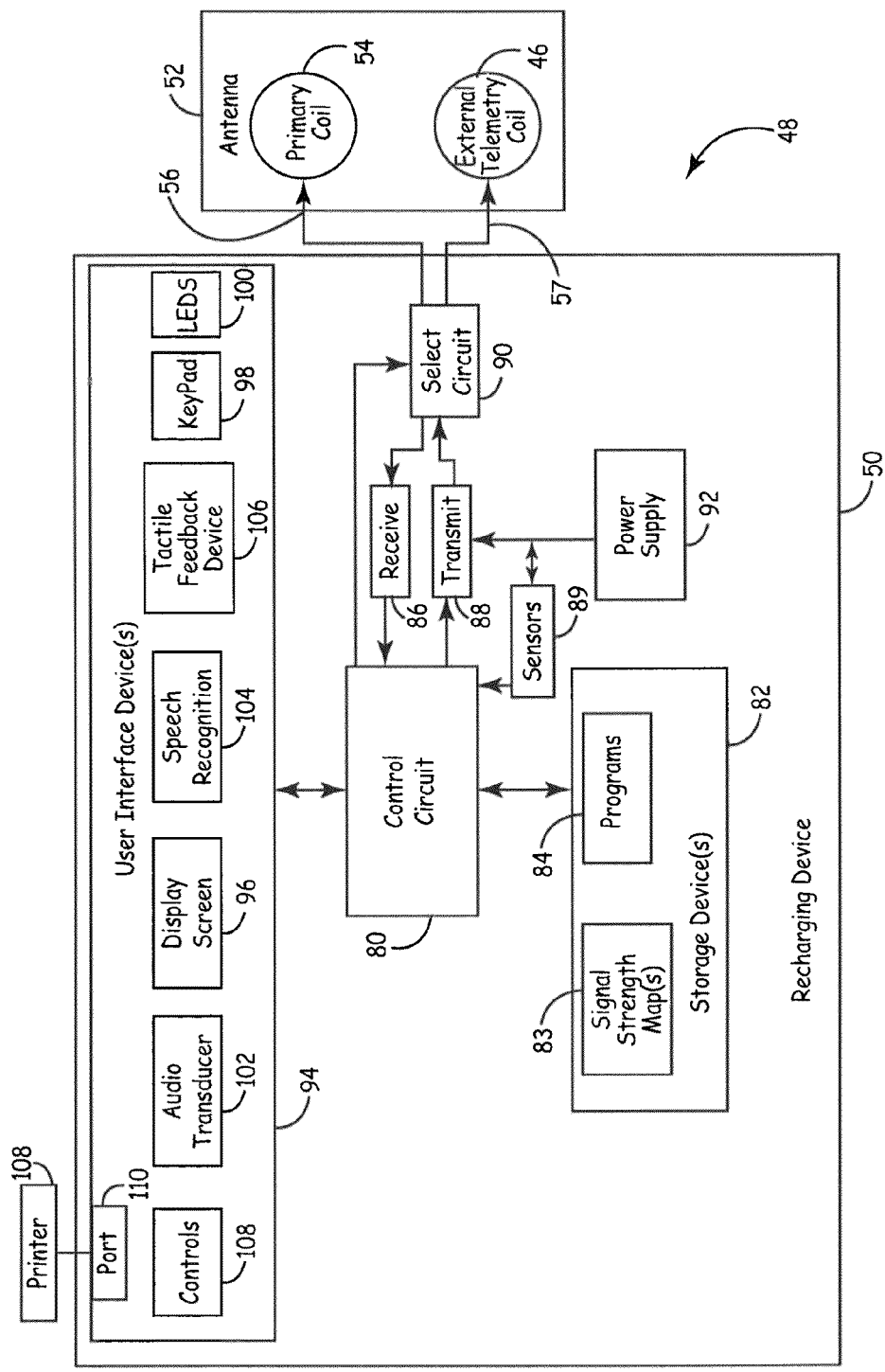
FIG. 4 is a block diagram of one embodiment of a recharging device and an antenna.

FIG. 4 is a block diagram of one embodiment of recharging unit 48. As shown in FIG. 3, recharging unit 48 includes recharging device 50 coupled to antenna 52. Antenna 52 includes primary coil 54 and external telemetry coil 46.

Recharging device 50 includes a control circuit 80, which initiates and controls recharging sessions with IMD 16. Control circuit 80 also initiates and controls telemetry sessions between recharging device 50 and telemetry circuit 47 of IMD 16. Control circuit 80 may include one or more microprocessors, FPGAs, ASICs, DSPs, microsequencers, discrete components, and/or other electronic circuit components.

Control circuit 80 is coupled to one or more storage device(s) 82. Storage device(s) 82 may include volatile, non-volatile, magnetic, optical, and/or electrical media for storing digital data and programmed instructions, including RAM, ROM, NVRAM, EEPROM, flash memory, removable storage devices, and the like. These storage devices may store software, firmware, and/or other types of programs 84 for use in controlling operation of control circuit 80. Storage device(s) may also store programmed parameters and data structures. According to the current invention, storage device(s) may store one or more signal strength maps 83, as will be discussed further below in reference to the current invention.

Control circuit 80 is also coupled to a communication circuit. In one embodiment, this communication circuit includes both a receive circuit 86 and a transmit circuit 88. Control circuit 80 initiates and controls telemetry sessions with IMD via these channels. Both receive circuit 86 and transmit circuit 88 may operate according to RF telemetry techniques such as IEEE 802.11 or Bluetooth specification sets, or may instead operate according to infrared communication as dictated by the IRDA specification set. Other standard or proprietary telemetry protocols may be used instead.

Transmit circuit 88 generates modulated electrical signals that are transferred to external telemetry coil 46 for electromagnetic transmission to internal telemetry coil 44 of IMD 16. Telemetry circuit 47 of IMD 16 receives and demodulates the modulated electrical signals and provides these signals to control circuit 49 of IMD 16 for use as configuration parameters, commands, status, software programs, and the like. Conversely, control circuit 49 of IMD 16 may provide commands, parameters, and/or data to telemetry circuit 47, which modulates the information, and transfers the modulated signals via internal telemetry coil 44 to external telemetry coil 46 of recharging unit 48. Receive circuit 86 demodulates these signals and provides the demodulated data to control circuit 80. In this manner, communication may occur between recharging unit 48 and IMD 16.

Within recharging device 50, both receive circuit 86 and transmit circuit 88 are coupled to antenna 52 via select circuit 90. Select circuit 90 may include one or more electronic switching components that are controlled by control circuit 80. Control circuit 80 may configure select circuit 90 so that either receive circuit 86 or transmit circuit 88 is coupled to telemetry coil 46 to facilitate telemetry communication in the manner discussed above.

Control circuit 80 may also configure select circuit 90 such that transmit circuit 88 is coupled to primary coil 54, as will be the case during a recharge session. When configured for recharge in this manner, transmit circuit 88 generates a current in primary coil 54 to inductively couple primary coil 54 to secondary coil 34 of IMD.

Transmit circuit 88 may include an H-bridge circuit powered from a power supply 92, which may be a 12-volt supply. This H-bridge circuit may receive control and timing signals from control circuit 80. In one embodiment, when select circuit 90 is configured to couple transmit circuit 88 to recharge coil 54, H-bridge circuit drives primary coil 54 at a selected recharge frequency, which may be 9 kHz or some other frequency. During telemetry, H-bridge circuit instead drives telemetry coil 46 at a selected communication frequency, which may be 175 kHz or another selected frequency.

In one embodiment, control circuit 80 may configure select circuit 90 such that transmit circuit 88 is coupled to recharge coil 54 at the same time as receive circuit 86 is coupled to telemetry coil 46. This allows an uplink session to be conducted while recharge is occurring, as will be discussed in detail below.

Primary coil 54 and external telemetry coil 46 may be of many different shapes and sizes. Both coils may be the same shape, or the coils may be different in shape. Either or both coils may be rectangular, circular, triangular, or some other shape. Either coil may be larger than the other, or both may be the same size. If desired, the coils may be co-axial with each other or with one or more of secondary coil 34 and/or external telemetry coil 44 of IMD 16, but this need not be the case. For purposes of the current invention, what is important is that when antenna 52 is in a stationary position proximate IMD 16, a telemetry signal received by external telemetry coil 46 from internal telemetry coil 44 has a signal strength that reliably corresponds with a recharge coupling efficiency between primary coil 54 and secondary coil 34 at that position. This will be discussed further below.

Control circuit 80 is further coupled to one or more user interface devices 94. Such user interface devices may include a display screen 96 such as a LCD or LED display that displays information for a user. In some embodiments, display screen 96 may be a touch screen display, and a user may interface with recharging unit 48 via peripheral pointing devices, such as a stylus or mouse.

User interface device(s) 94 may alternatively or additionally include a keypad 98, which may be employed by a user to interact with recharging unit 48. Keypad 98 may take the form of an alphanumeric keypad or a reduced set of keys associated with particular functions. If desired, a speech recognition device 104 may be utilized to allow recharging device 50 to have voice-activated capabilities.

User interface device(s) 94 may have various other mechanisms to communicate status and information to a user. For instance, one or more LEDs 100, such as those configured in an LED array, may provide visual feedback to an operator of recharging unit 48. An audio transducer 102 may be provided to generate one or more tones, which optionally may be generated at varying volumes. Audio transducer 102 may also have the ability to generate recognizable speech to aid a user who is visually impaired. A tactile feedback device 106 may be included to generate a vibration to an operator of recharging device 50, as described in U.S. Pat. No. 6,752,155 to Behn entitled "Tactile Feedback for Indicating Validity of Communication Link with an Implantable Medical Device". Yet another example of a user interface device may be a printer 108 that may be coupled to recharging device 50 via a port 110 such as a Universal Serial Bus (USB) port, or some other type of port capable of interfacing to a printer. Use of user interface device(s) in conjunction with the current invention is discussed further below.

Control circuit 80 may also be coupled to one or more sensors 89. These sensors may monitor power supply 92 or aspects of antenna 52. For instance, sensors 89 may measure the current being supplied to primary coil 54 and/or may measure voltage associated with this coil. Such measurements may be used to determine power being supplied to primary coil 54, as will be discussed below.

As is discussed above, recharging unit 48 is employed during a recharge session to recharge rechargeable power source 24. To provide for optimal energy transfer during a recharge session, it is important that primary coil 54 of recharging unit 48 be optimally positioned with respect to secondary coil 34 of IMD 16. One conventional way to do this is to locate the position of antenna 52 that results in a maximum current being induced in secondary coil 34. To begin this process, patient 18 or a clinician will choose a location on, or near, the patient's skin that is thought to align primary coil 54 with secondary coil 34. The patient or clinician may then use one of the user interface device(s) 94 such as controls 108 to initiate a recharge session. This will prompt control circuit 80 to couple transmit circuit 88 to primary coil 54 such that a current will be generated in the primary coil to inductively couple this coil to secondary coil 34. The resulting current within secondary coil 34, and/or a voltage across this coil, may be measured by a circuit within charging regulation module 42 such as sensors 35.

Periodically, control circuit 80 within recharging device 50 may reconfigure select circuit 90 so that transmit circuit 88 is coupled to external telemetry coil 46. Control circuit 80 then initiates a telemetry session with IMD 16, as may be accomplished by sending a wake-up pulse to IMD 16. This pulse will be detected by telemetry coil 44 of IMD and will prompt control circuit 49 of IMD to transmit a response back to recharging device 50. This response contains the current and/or voltage measurement(s) that were obtained during the recharge session and that are associated with the secondary coil 34. In a conventional system, recharging device 50 may utilize these measurements to determine whether adequate recharge coupling efficiency has been achieved, or whether antenna 52 should be repositioned. As discussed above, recharge coupling efficiency relates to how well the primary and secondary recharge coils are being coupled to one another. In one embodiment of the invention, the coupling is inductive. However, other types of electromagnetic coupling may be used in other embodiments.

Once a metric indicating recharge coupling efficiency has been established, it may be provided to the patient or clinician via one or more of user interface devices 94, such as via display screen 96. If necessary, the patient or clinician may then adjust the position of antenna 52 in attempt to increase the coupling efficiency. The recharge session may be re-initiated and the process repeated.

The foregoing conventional mechanism for determining whether adequate recharge coupling has been established is time-consuming. A considerable amount of time elapses while discontinuing a recharge session, initiating a telemetry session, obtaining the measurements from IMD 16, determining whether adjustments are necessary, repositioning antenna 52 as needed, and re-initiating the recharge session. Moreover, this process does not occur in real-time. That is, feedback is not available to aid in the repositioning activity, but is only available a substantial amount of time after the repositioning occurs.

The current invention provides techniques to support real-time feedback for positioning of antenna 52. These techniques utilize telemetry field strength as a surrogate for recharge coupling efficiency. According to one embodiment, the strength of a telemetry transmission provided by telemetry coil 44 of IMD and received by telemetry coil 46 of recharging unit 48 is measured. If the signal strength is at least as great as some predetermined threshold signal strength value that reliably corresponds with a minimum required recharge coupling efficiency, it is known that recharge may be initiated. Otherwise, a user is prompted to reposition an antenna, another telemetry transmission is received from IMD 16, and the process is repeated.

According to the current invention, feedback regarding antenna position occurs substantially in real time. That is, while the antenna is being positioned, the user receives feedback that indicates whether the current position is adequate, or whether repositioning is necessary. Once an adequate position is located, the user maintains the antenna at the position and recharging is initiated.

The current invention utilizes the fact that, in general, as telemetry coupling improves, recharge coupling will also improve. This is generally true because the primary coil 54 and the external telemetry coil 46 are contained in the same housing in relatively close proximity to one another. These coils may even be co-axial, and/or of similar shapes and sizes. Moreover, the secondary coil 34 and the internal telemetry coil 44 are likewise positioned relatively close to one another within, or in association with, IMD 16. Coils 34 and 44 may be co-axial, and/or may be of similar shapes and sizes.

Techniques described herein develop a correlation between signal strength of a telemetry transmission between an IMD and recharging unit and the recharge coupling efficiency that may exist between those two devices. Such a correlation may be developed empirically as antenna 52 of recharging unit 48 is positioned at various points relative to IMD 16 and both telemetry signal strength and recharge coupling efficiency are measured. This correlation between telemetry signal strength and recharge coupling efficiency may be recorded using a signal strength map. Hereinafter, a signal strength map refers to a mechanism for recording a correlation between telemetry signal strengths and recharge coupling efficiencies for a given IMD/recharging unit device pair. In one embodiment, a signal strength map may be implemented as one or more tables that perform the correlation between telemetry signal strengths and recharge coupling efficiencies. Other forms of signal strength maps, such as graphs, topological depictions, or other tools may be used instead of, or in addition to, tabular signal strength maps.

FIG. 5 is a table illustrating one embodiment of a signal strength map. In this example, the signal strength map is presented in the form of a table. A first column 150 of the table provides a metric that is indicative of telemetry signal strength. A second column 152 lists a second metric indicative of recharge coupling efficiency. The measurements and/or calculations used to derive these metrics, and the units in which the metrics are expressed, will be described further below. For current purposes, it is important to note that there is a reliable correspondence, which may be a one-to-one correspondence, between any given telemetry signal strength value appearing in column 150 and a corresponding recharge coupling efficiency metric in column 152 that is included within the same data set, or row, of the table. Because of this reliable correlation, a given telemetry signal strength value may be used to determine whether a recharge session may be established between recharging unit 48 and IMD 16.

Use of a signal strength map is best illustrated by example. Assume that a user is attempting to initiate a recharge session. Antenna 52 of recharging unit 48 is positioned proximate to IMD 16. A telemetry session is established between recharging device 50 and IMD 16. During this session, one or more measurements are taken that are indicative of the telemetry signal strength. These measurements are used to derive a value for telemetry signal strength. For purposes of this example, it is assumed that this signal strength value is expressed using the same metric as that used to describe the values appearing in column 150 of the signal strength map.

Assume a value of "31" is derived for telemetry signal strength in a manner to be discussed below. The exemplary signal strength map of FIG. 5 is referenced to find a data set in that map that contains, or most closely approximates, this derived value. In this example, data set 156 is located. This data set shows that a telemetry signal strength of "31" corresponds to a recharge coupling efficiency of 0%. Because a recharge coupling efficiency of "0%" is not acceptable for initiating a recharge session, the user is provided feedback indicating antenna 52 must be moved to a new position. As the antenna is repositioned, one or more new telemetry signal strength measurements may be obtained and another telemetry signal strength value derived. The user is then provided with additional feedback regarding this new antenna position. This feedback is able to be provided substantially in real-time because there is no need to initiate recharge, obtain recharge measurements, discontinue recharge, initiate a communication session, and communicate the recharge measurements to a recharging unit, as is the case in conventional systems.

Using the above-described techniques, the user will eventually position antenna 52 so that the derived telemetry signal strength metric corresponds with an adequate recharge coupling efficiency. As such, recharging unit 48 may signal the user to maintain antenna 52 at the current position. Control circuit 80 of recharging unit 48 may then automatically initiate a recharge session with IMD 16. Alternatively, recharging unit 48 may prompt the user to initiate the recharge session. For instance, the user may be prompted to depress a button on keypad 98 or a control mechanism on antenna 52 that will cause the recharge session to begin.

To further illustrate the foregoing, assume it has been determined that recharging should not be initiated until recharge coupling efficiency is at least 70%. In other words, a recharge coupling efficiency of "70%" is considered the threshold value needed to initiate a recharge session. This determination may be recorded within, or in conjunction with, the signal strength map. For instance, a flag may be stored in the signal strength map that identifies data set 158 as containing the recharge coupling efficiency threshold of 70%. Alternatively, a header block or some other control structure of the signal strength map may identify the recharge coupling efficiency of 70% as being the threshold value. Many other embodiments are possible for use in recording this information.

Once the recharge coupling efficiency threshold is selected, the corresponding telemetry signal strength threshold value is also known. In the current example, this threshold value is "128", as identified by data set 158. Because the telemetry signal strength values are directly proportional to the recharge coupling efficiency values, it is known that as long as the telemetry signal strength value is measured to be 128 or greater, adequate recharge coupling efficiency will be achieved and a recharge session may therefore be initiated.

Before continuing, it may be noted that in the signal strength map of FIG. 5, the telemetry signal strength metric of column 150 is directly proportional to the recharge coupling efficiency listed in column 152. This need not be the case, however. In another embodiment, a telemetry signal strength metric that is inversely proportional to the selected recharge coupling efficiency metric of column 152 may be used instead. In this case, the telemetry signal strength metric of column 150 must reach a value that is "less than, or equal to", a telemetry signal strength threshold value before recharge coupling may be adequately established. Thus, it should be recognized that the specific relationship existing between a selected telemetry signal strength metric and a recharge coupling efficiency metric may vary between embodiments, and is not important. What is important is that a correlation exists between the two metrics so that telemetry signal strength can be relied upon as a surrogate when determining whether adequate recharge coupling may be achieved.

The table of FIG. 5 includes fewer than a dozen data sets. This is for ease of reference only. It will be understood that a typical signal strength map may contain many more data sets, each including a telemetry strength signal value and a corresponding recharge coupling efficiency value. Next, several methods are described for using signal strength maps according to the current invention.

Figure 6:
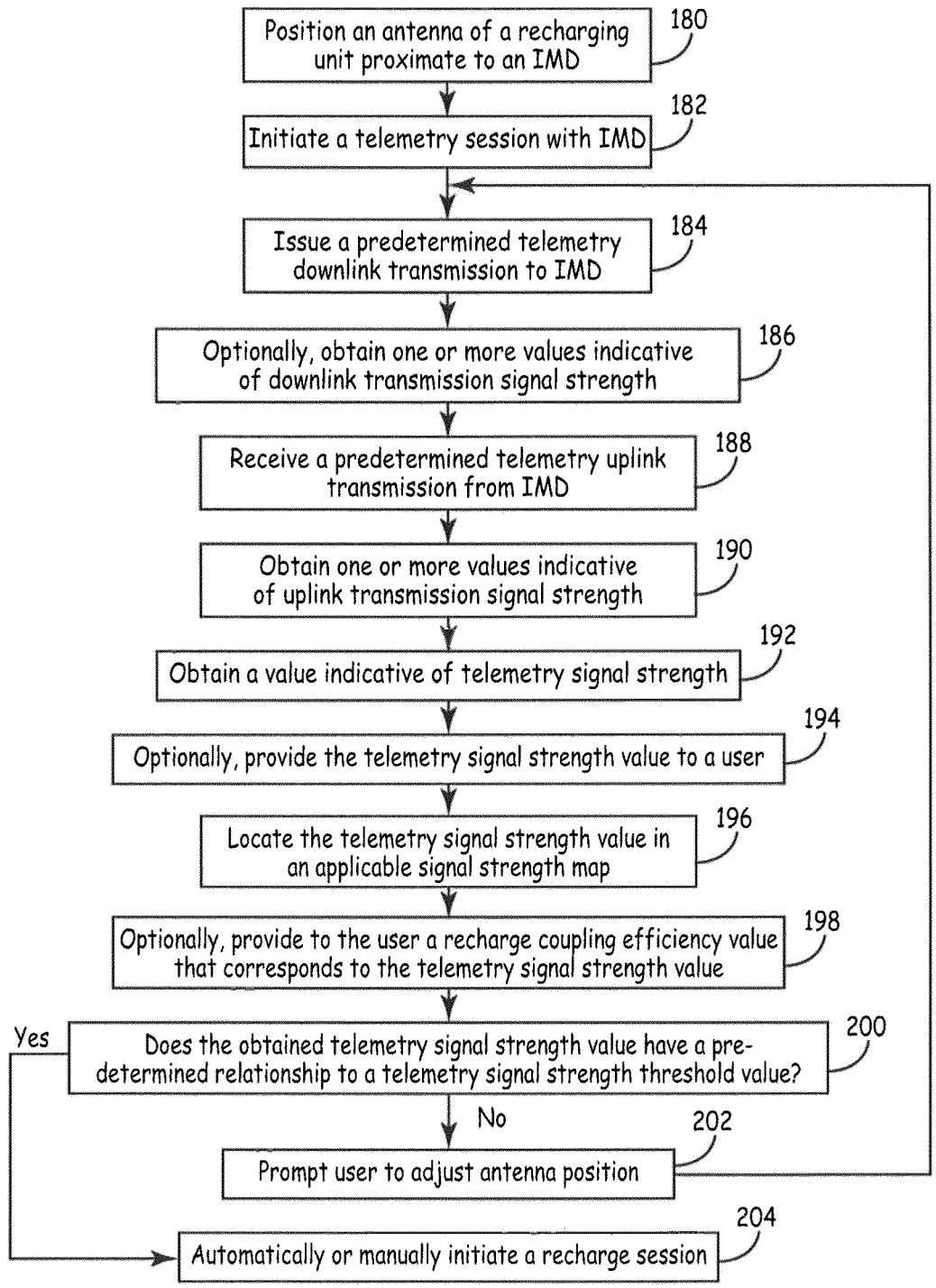
FIG. 6 is a flow diagram illustrating one method of using a signal strength map according to the current invention.

FIG. 6 is a flow diagram illustrating one method of using a signal strength map according to the current invention. First, an antenna 52 of a recharging unit 48 is positioned proximate to IMD 16 (180). A telemetry session is then initiated between recharging unit 48 and IMD 16 (182). This may be accomplished by issuing a wake-up pulse from the recharging unit 48 to the IMD 16, for instance. The IMD may then respond with an acknowledgement indicating that a telemetry session has been established.

Next, recharging unit 48 may issue a predetermined downlink transmission to IMD 16 that indicates a telemetry signal strength determination is being made (184). In one embodiment, this may cause IMD 16 to obtain one or more values indicative of the strength of the telemetry signal during the downlink transmission (186). This will be discussed further below.

The downlink transmission prompts IMD 16 to respond with a predetermined telemetry uplink transmission, which is received by recharging unit 48 (188). In one embodiment, this uplink transmission may include the one or more values indicative of the downlink telemetry signal strength that were obtained by the IMD.

During, or after, the uplink transmission, recharging unit 48 may obtain one or more values that are indicative of the signal strength of the uplink transmission (190). At least one of the values indicative of the uplink transmission signal strength and/or downlink transmission signal strength are then used to derive or obtain a value indicative of the telemetry signal strength generally (192). For instance, a value indicative of an average between uplink and downlink signal strength may be derived. This telemetry signal strength value may optionally be provided to a user for informational purposes (194). This information may be provided to a user via one of user interface devices 94 (FIG. 4), for instance.

An applicable signal strength map may be referenced to locate the telemetry signal strength value that was obtained in step 192 (196). The signal strength map that will be used for this purpose will generally be specific to the type of IMD as well as the type of recharging unit 48 that are involved in the recharge session. This will be discussed below.

As an example of step 196, assume that a telemetry signal strength value of "128" has been derived from the downlink and/or uplink signal strength values obtained in steps 186, and 190, respectively. Further assume that the applicable signal strength map that applies to the IMD/recharger device pair is the table shown in FIG. 5. Accordingly, value 128 may be located in data set 158 of this signal strength map.

Next, a corresponding value of "70%" describing recharge coupling efficiency may be obtained from data set 158 of the signal strength map. This value may optionally be provided to the user for information purposes (198), as may be accomplished using one or more of user interface devices 94 (FIG. 4).

The obtained telemetry signal strength value may then be compared to a predetermined threshold signal strength threshold value to determine whether the telemetry signal strength value has a predetermined relationship to the threshold value (200). As discussed above, this threshold value is somehow identified by the signal strength map. This may be accomplished by identifying the data set storing this threshold value, by storing the value in a header or another control structure of the signal strength map, or by some other means.

In addition to identifying the telemetry signal strength threshold value, the signal strength map may also identify the "predetermined relationship" that is to be used by control circuit 80 along with the map to determine whether this threshold value has been met. For instance, the signal strength map may store a flag or some other value that indicates whether the predetermined relationship is "greater than, or equal to", "less than, or equal to", "greater than", "less than", or some other relationship. Control circuit 80 may extract this value that determined the "predetermined relationship" from the signal strength map and adjust processing associated with step 200 accordingly.

To simplify the current discussion concerning comparison step 200, it will be assumed that the telemetry signal strength metric that is in use is directly proportional to the recharge coupling efficiency in the manner illustrated in FIG. 5. Thus, it will be assumed that for this example, processing associated with step 200 will determine whether the telemetry signal strength value is "greater than, or equal to" the threshold value for telemetry signal strength. If the telemetry signal strength value is not greater than, or equal to, the threshold value, the user will be directed via feedback to adjust the position of antenna 52 (202). This feedback may be provided via one or more of the user interface devices 94 of FIG. 4. On the other hand, if the telemetry signal strength metric does have the predetermined relationship (e.g., "greater than, or equal") to the threshold value, a recharge session is initiated (204). This may occur after the user has been directed to maintain the antenna at the desired position, and may be initiated automatically, as by control circuit 80, for example. Alternatively, the user may be prompted to manually initiate this session.

As previously discussed, the "predetermined relationship" of step 200 need not be "greater than, or equal to", as is the case in the example above. If the signal strength metric has an inversely proportional relationship to recharge coupling efficiency, the predetermined relationship that must exist prior to the initiation of recharge will instead be "less than, or equal to".

The current invention provides a very efficient mechanism for positioning antenna 52 relative to IMD 16 prior to establishing a recharge session. Obtaining and evaluating a telemetry signal strength metric may be accomplished virtually in real-time as the antenna is repositioned. Thus, the user is able to locate an optimal recharging position very quickly, and without the need to repeatedly initiate, and then interrupt, recharge sessions.

One skilled in the art will appreciate that many alternative embodiments are possible for the method of FIG. 6. For instance, in FIG. 6, each uplink transmission from the IMD 16 (step 190) is preceded by a corresponding downlink transmission to the IMD 16 (step 184). In one embodiment, the downlink transmission may be eliminated. In this embodiment, once a telemetry session has been established for antenna positioning purposes, the IMD may continuously send out uplink telemetry transmissions that are unprompted. This type of embodiment is described in reference to FIG. 7.

Figure 7:
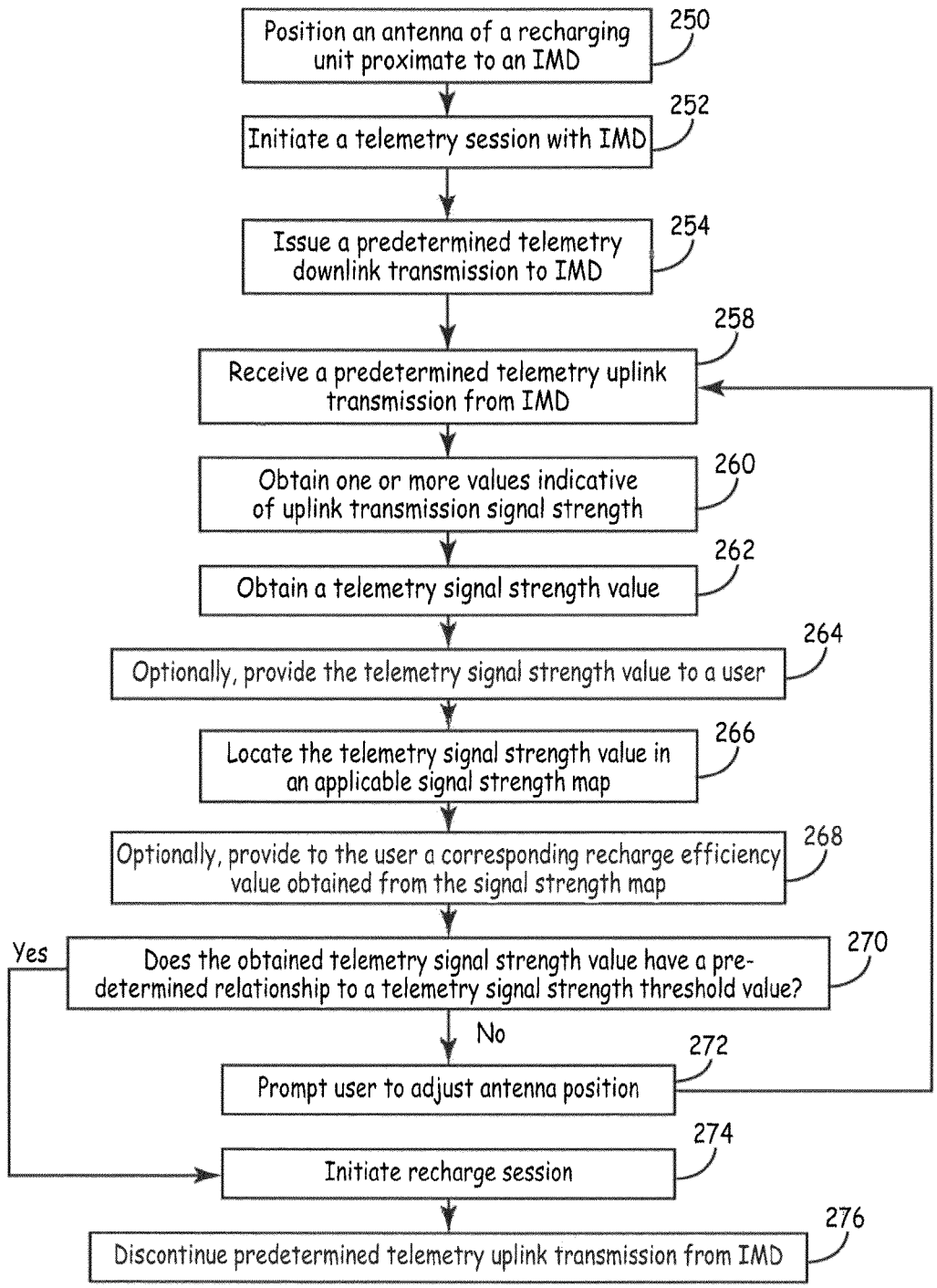
FIG. 7 is a flow diagram illustrating another method of using a signal strength map according to the current invention.

FIG. 7 is a flow diagram illustrating another method of using a signal strength map according to the current invention. Antenna 52 of a recharging unit 48 is positioned proximate to IMD 16 (250). A telemetry session is then initiated with IMD 16 (252). Recharging unit 48 may then issue a predetermined downlink transmission to IMD 16 that indicates a telemetry signal strength determination is being made (254). IMD 16 next responds with either a continuous, or non-continuous, stream of telemetry uplink transmissions to recharging unit 48 (258). Upon receipt of such an uplink transmission, recharging unit 48 obtains one or more values indicative of the signal strength for that uplink transmission (260). At least one of the values indicative of uplink transmission signal strength is used to obtain a value indicative of telemetry signal strength generally (262). This telemetry signal strength value may optionally be provided to a user for informational purposes (264), as via one or more of user interface devices 94 (FIG. 4).

An applicable signal strength map may be referenced to locate the telemetry signal strength value (266). The signal strength map that will be referenced for this purpose will generally be specific to the type of IMD as well as the type of recharging unit 48 involved in the recharging session.

After the telemetry signal strength value is located within the signal strength map, a corresponding value describing recharge efficiency may optionally be obtained from the signal strength map and provided to the user for informational purposes (268). The signal strength map may further be used to determine whether the telemetry signal strength value has a predetermined relationship to some predetermined signal strength threshold value (270). If not, the user is prompted to adjust the position of antenna 52 (272).

According to the current embodiment, after the user adjusts the antenna position, the process continues with step 258, where either a continuation of the same, or another, uplink transmission is received from the IMD 16. In this embodiment, no corresponding downlink transmission is provided to prompt this uplink transmission. Following receipt of the uplink transmission, another telemetry signal strength value is obtained (262), and the signal strength map is used to evaluate the adequacy of the current antenna position.

Returning to step 270, if it is determined that the telemetry signal strength value does have a predetermined relationship to the signal strength threshold value (e.g., such as "greater than, or equal to"), a recharge session is initiated (274). This may occur either automatically, or by prompting a user to manually perform this step. The initiation of a recharge session may further prompt the IMD to discontinue the telemetry uplink transmission(s) to IMD 16 (276).

The embodiment described in FIG. 7 may be more efficient than that discussed in FIG. 6 because the steps of issuing a downlink telemetry transmission (step 184 of FIG. 6) and optionally obtaining downlink signal strength metrics (step 186 of FIG. 6) are eliminated. However, a continuous uplink telemetry transmission from IMD 16 may, if allowed to continue for an extended period of time, further drain rechargeable power source 24, which is undesirable. Therefore, as one variation of the method of FIG. 7, the uplink telemetry session may only continue unprompted for a predetermined period of time. In one embodiment, that time period is programmable. After the expiration of this time period, another downlink telemetry transmission will be required to prompt IMD 16 to again begin re-transmitting the uplink telemetry transmission for antenna positioning purposes.

In the methods of FIGS. 6 and 7, once recharge is initiated, uplink telemetry transmissions are not employed. For example, step 276 of FIG. 7 specifically discontinues telemetry uplink transmission upon the initiation of a recharge session. This may be necessary because in some circuit designs, the initiation of a recharge session via transmit circuit 88 may result in noise within receive circuit 86 that prohibits receipt of an error-free telemetry uplink transmission. In a system wherein this is not the case, however, IMD 16 may continue to periodically issue uplink telemetry transmissions after a recharge session has been established. These uplink telemetry transmissions may be used to determine whether antenna 52 has been maintained at a position that allows recharging to occur in an efficient manner. This embodiment is discussed in reference to FIG. 8.

Figure 8:
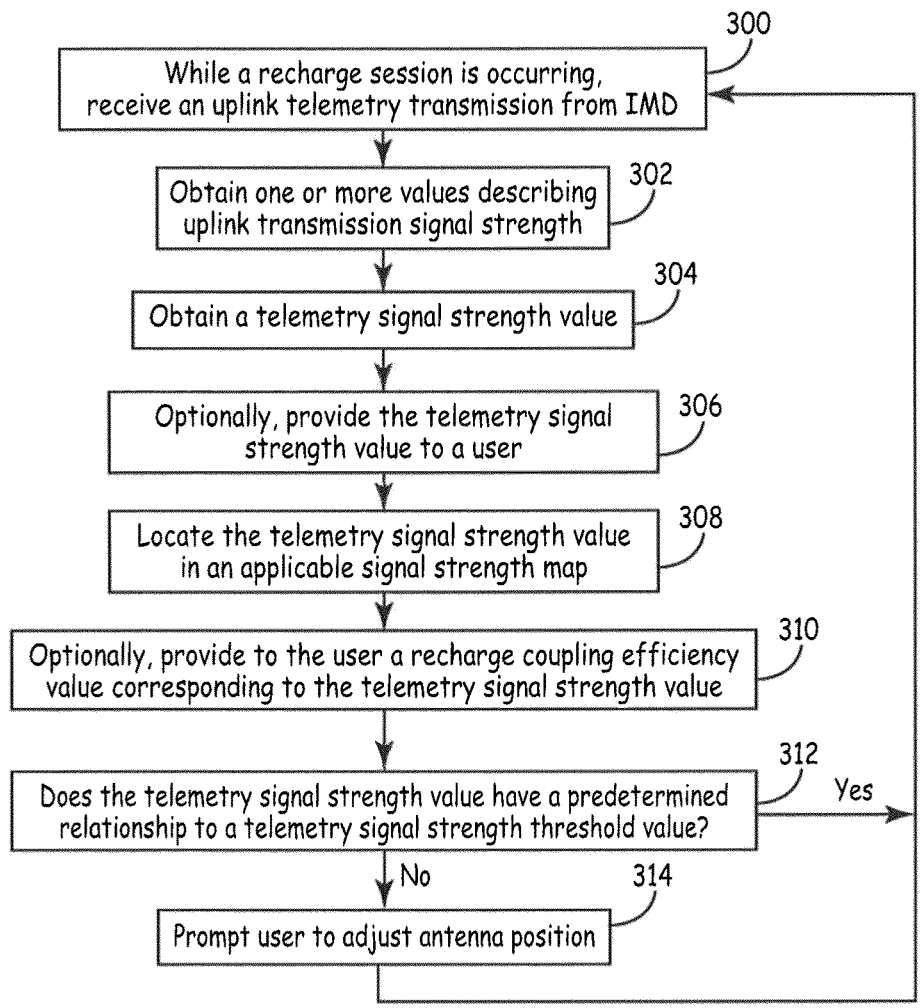
FIG. 8 is a flow diagram of an embodiment of the invention that provides for adjustment of an antenna position after a recharge session has been established according to the current invention.

FIG. 8 is a flow diagram of an embodiment of the invention that provides for adjustment of the antenna position after a recharge session has been established according to the current invention. This may be useful if the position is inadvertently altered somewhat during the recharge session. According to this method, while a recharge session is occurring, an uplink telemetry transmission continues to be received by recharging unit 48 from IMD 16 (300). One or more values describing uplink transmission signal strength are obtained (302) and used to further obtain a telemetry signal strength value (304). This value may optionally be provided to a user for informational purposes (306).

The telemetry signal strength value may be located in an applicable signal strength map (308). A recharge coupling efficiency value that corresponds to the telemetry signal strength value may be retrieved from the signal strength map and provided to the user for informational purposes (310). Finally, it is determined whether the telemetry signal strength value has a predetermined relationship (e.g., "greater than, or equal to") to a telemetry signal strength threshold value (312). If so, the process is merely repeated by returning to step 300 and waiting for another uplink telemetry transmission. No adjustment is required. Otherwise, the user is prompted to adjust the position of antenna 52 (314). The recharge session may continue during the adjustment process, which includes returning to step 300 to obtain another uplink transmission so that another determination may be performed. In another embodiment, the recharge session may be discontinued if decision step 312 is negative. In this latter embodiment, recharge is not reinitiated until a satisfactory recharge coupling efficiency has been re-established by repositioning antenna 52. In either embodiment, the process of FIG. 8 may be carried out until recharge of the IMD has been completed.

The techniques discussed herein depend on providing some feedback to a user, who may be a clinician or a patient. This feedback will indicate whether an antenna is adequately positioned to initiate recharge, or instead must be repositioned. One or more types of user interface devices are available to provide this feedback. Some examples of user interface device(s) are shown in the system block diagram of FIG. 4, although these examples are not exhaustive.

User interface devices 94 include a display screen 96 which may be used to provide the user with a message and/or other data indicating whether recharge may be initiated. For instance, display screen 96 may provide the telemetry signal strength value and/or the recharge coupling efficiency value from columns 150 and 152 of FIG. 5 that correspond to a current position of the antenna. The display may also optionally indicate the threshold values and/or optimal values for comparison purposes. This may be employed by a user to determine whether the current antenna position is close to the optimal position. As an example, in reference to FIG. 5, the display may indicate that the maximum achievable recharge coupling efficiency is 86%. This allows the user to understand that once this efficiency has been achieved, the positioning is optimal and cannot be improved.

FIGS. 9A and 9B are screen shots of exemplary display screens that may be generated to provide feedback to a user according to the current invention. In particular, FIG. 9A is an illustration of a screen shot that may be provided when the antenna is positioned such that adequate recharge coupling has not yet been obtained. The screen provides instructions prompting a user to reposition the antenna. The screen also provides quantified feedback as to the coupling efficiency achieved so far. In this example, the currently-measured ("current") coupling efficiency is listed as 10%. The minimum threshold value that is required to initiate a recharge session ("min") and the optimal recharge coupling efficiency value ("max") are also provided for informational purposes in this display. For example, in FIG. 9A, it is assumed that a recharge session cannot be initiated until the threshold value of 70% recharge coupling efficiency is achieved. The maximum recharge coupling efficiency that can be achieved is 86% in this example. These values correspond to the above examples described in reference to the signal strength map of FIG. 5.

FIG. 9B is an illustration of a screen shot provided after the antenna is positioned so that adequate recharge coupling may occur. The screen provides a message indicating that recharge has been initiated because the current recharge efficiency is adequate. Additional information may be provided to indicate the recharge coupling efficiency at the current antenna position ("current"), which is 80% in the example. The minimum recharge efficiency of 70% that is required to initiate recharge ("min"), and the maximum possible recharge coupling efficiency of 86% ("max") are also provided for informational purposes.

If desired, colors, icons, and/or other types of visual aids may be used to enhance the usability of the screen display. For instance, the screen information shown in FIG. 9A may be highlighted in red to indicate recharge has not yet been initiated. In contrast, the screen information of FIG. 9B may be provided in green to indicate recharge is proceeding. As another example, once recharge has been initiated, the information of FIG. 9B may be shown in a "blinking" format to convey that recharge is underway. Alternatively or additionally, a recharge icon such as a "lightening bolt" symbol may be displayed for the user to indicate that recharge is proceeding.

The screen shots of FIGS. 9A and 9B provide values pertaining to a recharge coupling efficiency metric that is expressed in terms of percentages. This corresponds to the exemplary metric provided in column 152 of FIG. 5. These screen shots may provide other metrics instead of, or in addition to, this type of recharge coupling efficiency metric. For instance, the metric from column 150 of FIG. 5 may be provided instead of, or in addition to, the metric from column 152. However, "raw" metrics indicative of telemetry signal strength are likely to be less intuitive to a user than a recharge coupling efficiency metric expressed in terms of a percentage.

FIGS. 9A and 9B provide a text message and data associated with efficiency. If desired, some other type of visual feedback may be provided to a user. For instance, a pie chart or some other type of graph may be used to represent either the telemetry signal strength metric or the recharge coupling efficiency metric. Icons may be used to indicate whether charging is occurring, as mentioned above. As yet another example, an array of LED "bars" may be provided to visually indicate strength of the measured telemetry signal strength and/or the associated recharging coupling efficiency.

As discussed above, user interface devices 94 may additionally or alternatively contain an audio transducer 102. This audio transducer may be used to generate tones corresponding to antenna position. For instance, the tones may be generated at progressively higher or lower pitches as the antenna becomes more optimally positioned relative to IMD 16. Alternatively or additionally, the tones may get progressively louder as the antenna is moved toward an optimal position. This type of feedback may benefit patients that are sight-impaired.

Audio transducer may include speech generation circuits that provide feedback using recognizable words or phrases. For instance, this type of system may audibly employ phrases such as "continue repositioning", or even "continue repositioning in the current direction". Such phrases may be used to indicate that control circuit 80 has determined that the telemetry signal strength metric is getting progressively closer to the threshold value. This system may further audibly indicate metrics, such as a percentage of coupling efficiency that corresponds to a current telemetry signal strength metric. This type of feedback may be helpful to a visually-impaired patient.

Still another exemplary type of user interface device that may be utilized includes a printer 108, which may be coupled to a port 110 such as a Universal Serial Bus (USB) port or some other type of interface. This port may be used to print a report of the telemetry signal strength metrics obtained prior to initiation of recharge. Such a report may be used as additional feedback to help a user become more adept at positioning an antenna during future recharge sessions. Such a report may also be used to diagnose positioning-related problems with recharging unit 48 or IMD 16.

Still another type of feedback mechanism is a tactile feedback device 106. Such a device may be used to generate vibrations when the antenna has been positioned so that the signal strength threshold has been obtained. This may aid a user that is both sight- and hearing-impaired.

FIGS. 9A and 9B contain information that is obtained by referencing a signal strength map in the manner discussed above. That is, a telemetry signal strength value is used to reference a signal strength map to obtain a corresponding recharge coupling efficiency value. This value may then be reported to a user. In one embodiment, this type of feedback that provides the user with information concerning the achieved recharge coupling efficiency may be eliminated. In this type of embodiment, the signal strength map need only be referenced once to retrieve the telemetry signal strength threshold value and the "predetermined relationship" that will be used to determine whether the threshold value has been met. This type of decision step is exemplified by step 200 of FIG. 6. Once this information has been retrieved from the signal strength map, no additional references to the signal strength map are needed. The user will be prompted to continue repositioning the antenna until the predetermined relationship has been found to exist, at which time recharge may be initiated. In such an embodiment, the signal strength map may be reduced to a single entry that merely stores the signal strength threshold value and the "predetermined relationship". This may be useful in a recharging unit containing limited storage space.

In yet another implementation wherein the "predetermined relationship" is the same for all signal strength maps in use (e.g., "greater than, or equal to"), a signal strength map may be reduced to a single entry that simply stores the telemetry strength threshold value.

The foregoing discussion describes how signal strength maps may be used to position an external recharge antenna prior to, or during, a recharge session. These mechanisms depend on having a signal strength map that provides a reliable correlation between telemetry signal strength values and recharging coupling efficiency. The following discussion focuses on the generation of these types of signal strength maps.

In general, signal strength maps may be obtained in several ways. According to one method, signal strength maps may be generated empirically using measurements taken as an antenna 52 is repositioned at various locations proximate to IMD 16. This type of empirical approach is considered in reference to FIG. 10.

Figure 10:
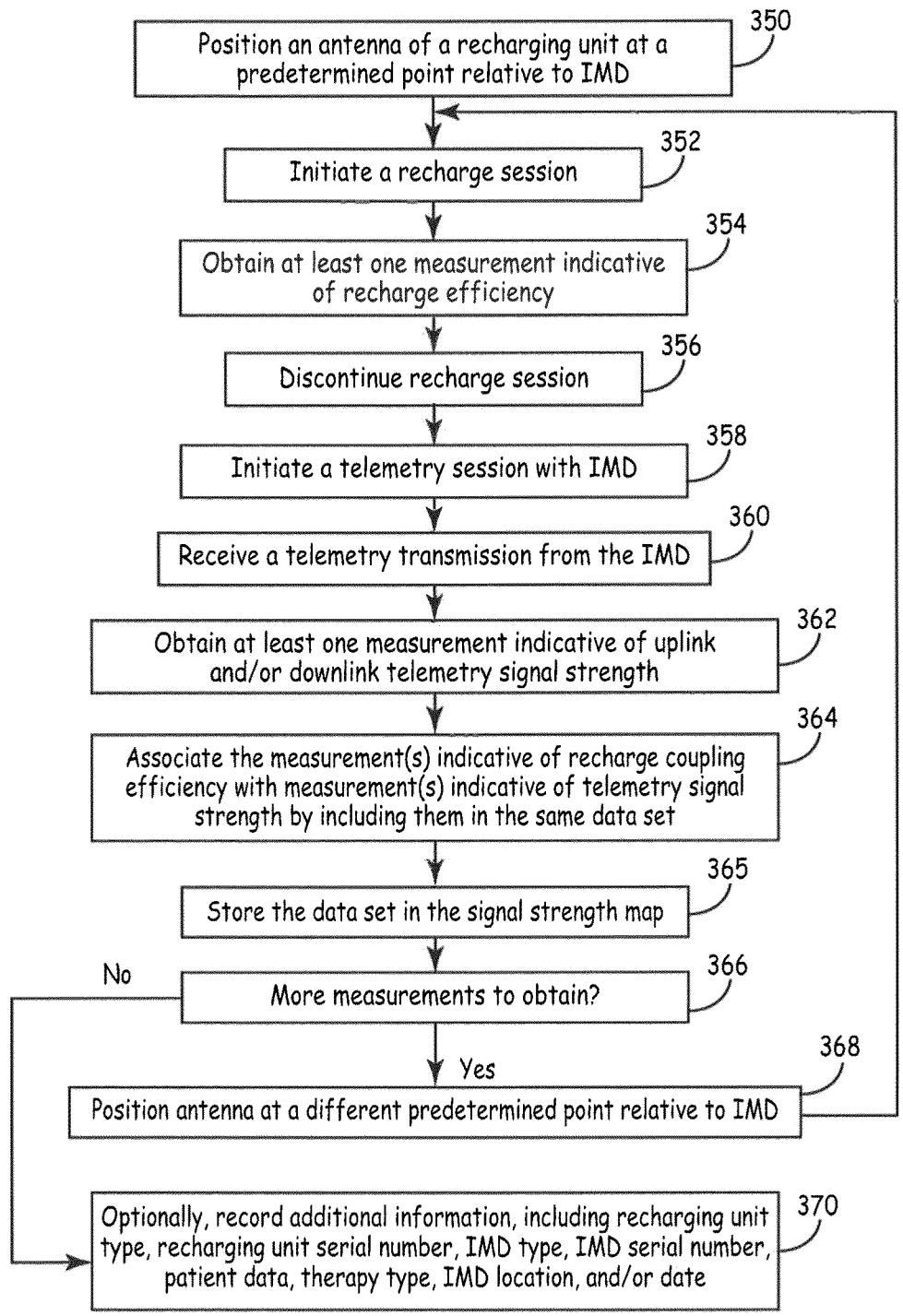
FIG. 10 is a flow diagram illustrating one method of using an empirical approach to obtain metrics to generate a signal strength map.

FIG. 10 is a flow diagram illustrating one method of creating a signal strength map using an empirical approach. The steps of this method may be performed either before or after an IMD is implanted in a patient. While the steps may be more conveniently performed prior to implant, more accurate results will be obtained if the steps are followed post-implant, as will be discussed further below.

First, antenna 52 of recharging unit 48 is positioned at a predetermined point relative to an IMD (350). For instance, if this procedure is being performed post-implant, antenna may be positioned on the patient's skin as closely as possible to the site of the implant. Next, recharging unit 48 initiates a recharge session with IMD 16 (352). During this recharge session, at least one measurement is obtained that is indicative of recharge efficiency (354). Such measurement(s) may include a measure of a current in, or a voltage across, primary coil 54, as may be obtained via sensors 89 (FIG. 4). These measurements may be provided to control circuit 80 for use in determining recharge efficiency. Another measurement may include the loading on the primary coil, which may be at a maximum when optimal inductive coupling has been achieved, assuming there are no metallic objects in the vicinity of the IMD to skew measurements. Yet other measurements may comprise current in, and/or voltage across, secondary coil 34 of IMD 16, as may be obtained by sensors 35 associated with recharge coil 34.

Once measurements are obtained, the recharge session may optionally be discontinued in preparation to initiate a telemetry session (356). This step of discontinuing the recharge session may be eliminated in an embodiment that allows the recharge session to continue while telemetry uplink and downlink transmissions are occurring.

Next, recharging device 50 initiates a telemetry session with IMD 16 (358). This may be accomplished, for example, by sending a wake-up pulse to telemetry circuit 47 of IMD 16. This wake-up pulse or some subsequent transmission issued by recharging device 50 may be employed to prompt IMD 16 to return an uplink telemetry transmission from IMD to recharging unit 48 (360). This uplink transmission may optionally include one or more measurements that were taken by IMD 16 as a measure of the recharge efficiency, as may be accomplished using sensors 35 in the manner discussed above. This transmission may further include a measurement of telemetry signal strength of the downlink telemetry transmission.

The uplink telemetry transmission provided by IMD 16 is received by recharging unit 48 (360). During receipt of this transmission, at least one measurement is obtained by recharging device 50 that describes the signal strength of at least one of the uplink or downlink telemetry transmission (362). In one embodiment, the measurement is a Received Signal Strength Indication (RSSI). As known in the art, RSSI is a generic receiver technology metric that is used in IEEE 802.11 and other telecommunication protocols. In particular, in an IEEE 802.11 system, RSSI provides the received signal strength in a wireless environment as expressed in arbitrary units. RSSI can be used by a communication system to determine when the amount of radio energy in a communication channel is below a certain threshold such that it may be considered "clear to send". This metric is generated by a receiving channel at the intermediate frequency (IF) stage, and may be expressed as a one-byte integer value ranging between 0 and 255. The RSSI value that will be generated for any given signal level is vendor-specific, and depends on the receiving circuitry.

In one embodiment, receive circuit 86 of recharging device 50 includes a circuit to generate an RSSI value for uplink telemetry transmissions. Receive circuit 86 incorporates the RSSI value into a control frame of the uplink transmission, which then is available for use in controlling a message transmission. For instance, receive circuit 86 will add an RSSI value to a control frame of a received telemetry transmission. The transmission is then forwarded to control circuit 80, which extracts the RSSI value for use according to the current invention. For instance, in one embodiment wherein control circuit 80 includes a microprocessor, the microprocessor extracts this RSSI value from the transmission for use as an indication of uplink signal strength.

The foregoing describes the signal strength indication as being an RSSI value obtained from an uplink communication. However, this need not be the case. The signal strength indication may instead be an RSSI value obtained by a receive circuit of telemetry circuit 47 of IMD 16 during a downlink transmission. The RSSI value may be provided via a subsequent uplink telemetry transmission to recharging device 50 for use as a signal strength measurement. For instance, this value may be included in the same uplink telemetry transmission that provides any measurements (e.g., current and/or voltage) that were obtained to indicate recharge efficiency. In yet another embodiment, a first RSSI value generated by the telemetry circuit 47 of IMD 16 and a second RSSI value obtained by receive circuit 86 may both be utilized to establish the signal strength indication. For instance, an average of the two RSSI values may be used for this purpose.

While one or more RSSI values may be used as measures of signal strength, signal strength may be determined by other techniques. For instance, U.S. Pat. No. 5,107,833 to Barsness describes a mechanism for monitoring signal strength based on a gain setting of the uplink receiver, such as that associated with receive circuit 86. If desired, this technique may likewise be used to measure downlink signal strength instead of, or in addition to, the uplink signal strength. An average of the downlink and uplink gains may be employed as the telemetry signal strength metric, if desired.

As may be appreciated, the gain of a receiver is inversely proportional to the signal strength. For instance, a lesser signal strength results in a higher gain being provided by receiver circuit 86, and vice versa. Thus, use of gain settings as a measure of telemetry signal strength metric will yield a metric that is inversely proportional to signal strength, and also inversely proportional to recharge coupling efficiency. This must be taken into accounted when using the signal strength map in the manner discussed above.

Other embodiments of the invention may utilize other indications of signal strength instead of, or in addition to, those indications discussed above to derive the telemetry signal strength metric.

After one or more telemetry signal strength measurements have been obtained in step 362, one or more metrics describing recharge coupling efficiency are associated with the one or more measurements describing telemetry signal strength (364). For example, one way to create this association is by including the associated measurements in the same data set, which may be the same entry, or row, of a table, as shown in the table of FIG. 5. The newly-created data set may then be stored within the signal strength map (365).

After an association is created between the recharge coupling efficiency measurement(s) and the corresponding telemetry signal strength measurement(s), it may be determined whether additional data sets are to be obtained for use in generating the signal strength map (366). If so, antenna 52 is repositioned to another predetermined point relative to IMD 16 (368). As an example, if the antenna had roughly been positioned directly over IMD 16, the antenna may be moved slightly off-center in a selected direction. Thereafter, processing returns to step 352 where another recharge session is initiated and another data set is obtained that includes at least one measurement indicative of recharge coupling efficiency and at least one associated measurement indicative of telemetry signal strength. Each set of measurements is contained in a different respective data set of the signal strength map.

The process described above is continued as antenna 52 is moved to various positions in the vicinity of IMD 16. For instance, the process may be initiated with antenna 52 positioned directly over the IMD 16. The antenna may then be moved systematically outward from the approximate center of the IMD in a chosen direction. Once a position is reached where no appreciable recharge coupling may be achieved, the antenna 52 may be repositioned over the center of the IMD and the process repeated by moving the antenna 52 outward in a different direction. In this manner, antenna can be thought of as being periodically repositioned at a hub of a wheel corresponding with the IMD location. Data sets are recorded as antenna 52 is systematically moved outward from this hub along spokes of this wheel.

In another variation of the foregoing procedure, antenna 52 may initially be centered substantially directly over IMD 16, and then systematically moved in a pattern approximating an enlarging spiral away from the center. Many other processes for obtaining data sets may be contemplated. What is important is that the measurements be obtained systematically so that the entire recharge field of IMD 16 is represented by the resulting signal strength map.

Once enough data sets have been recorded to create a comprehensive signal strength map as determining in step 366, the signal strength map may be updated to include additional information describing the signal strength map (370).

Such information may include an identification of the type of IMD 16 (e.g., make/model) involved in developing the signal strength map, a serial number of the IMD, type of recharging unit 48 (e.g., make/model) used to generate the signal strength map, a serial number of the recharging unit, patient data (e.g. patient name, implant date, etc.), and/or a date the signal strength map was created.

Of particular importance is information describing the IMD and recharging unit. Such information is important because the coupling achieved between an IMD and recharging unit is highly specific to the device pair. That is, the size, shape, and electrical characteristics of coils 34, 44, 46 and 54, as well as those same characteristics of IMD 16 and recharging unit 48 generally, will influence the measurements contained within the signal strength map. Thus, a particular signal strength map will likely be used with a specific IMD/recharger device pair.

According to the foregoing, a specific signal strength map may be developed for a given IMD/recharger device pair based on the model/make numbers of the two devices. For instance, a signal strength map designated "A/B/C/D" may be created that corresponds to an IMD/recharger pair wherein the IMD has a make/model of "A/B" and the recharging unit has a make/model of "C/D", This map may then be used with any instance of an IMD/recharger device pair involving this specific pair of devices.

A more precise approach will develop a signal strength map for each instance of an IMD/recharger device pair. This will take into account the various tolerances and permissible variations in the electrical circuitry within a given instance of an IMD and an instance of a recharging unit 48. For example, receive circuit 86 of recharging device 50 may include a circuit that assigns a received signal a RSSI value of "100", whereas a different instance of the same receive circuit may assign the same signal a RSSI value of "110" because of different acceptable tolerances of the circuitry. Similarly, measurements used to indicate recharge efficiencies, as obtained by sensors 89 and 35 within recharging device 50 and IMD 16, respectively, may vary based on permissible tolerances of the sensors. Any of the electrical components in the devices may be associated with tolerances that will affect the generation of the signal strength map, and therefore generating the map for each specific instance of an IMD/recharger pair will yield more accurate results.

If a unique signal strength map is created for each instance of an IMD/recharger device pair, it is generally desirable to record specific information to identify that device pair. Such information may include a serial number of IMD 16 and/or of recharging unit 48, data identifying the patient treated by the device pair, date of creation of the signal strength map, and/or other information identifying the map instance.

Alternatively, or additionally, a specific signal strength map may be created for a particular therapy and/or a particular implant site. This may be useful, since the therapy delivered by an IMD and/or the site of implant of the IMD may affect at least one of the implant depth of the IMD and orientation of the IMD. This, in turn, will affect recharge coupling efficiency. Thus, it may be desirable to develop signal strength maps that are specific to a particular implant site, therapy and/or patient.

As discussed above, a signal strength map and all associated information may be stored along with other signal strength map(s) 83 in storage device(s) 82 of recharging device 50. In one embodiment, a copy of the signal strength map may be transferred to IMD 16 during a telemetry session for storage as one of signal strength map(s) 53 retained by storage device(s) 51 of IMD. Additionally, or alternatively, a copy of the signal strength map may be stored within an external programmer or another external storage device, such as a removable external storage device containing flash memory or another type of storage media that may be removably coupled to port 110.

The foregoing method of creating a signal strength map may be performed pre-implant when IMD 16 is outside the body by moving antenna 52 within the vicinity of IMD 16 at distances approximating those that would exist post-implant. While this type of simulated environment develops a signal strength map that includes approximate measurements, more accurate measurements may be obtained if the signal strength map is instead created post-implant. This will allow the signal strength map to more accurately take into account particularities that are associated with each implant scenario. For instance, the depth of implant may vary from patient-to-patient depending on body types, a prescribed therapy, and the nature of the symptoms being treated by the IMD. Additionally, the orientation of IMD 16 within the patient's body may vary. For instance, it may not be positioned parallel to the cutaneous boundary. Finally, lead positioning and the presence of other therapeutic devices within the patient's body may affect the measurements taken to indicate recharging coupling efficiency and signal strength.

For the foregoing reasons, a more accurate signal strength map may be generated after implant has occurred in a manner similar to that discussed above. That is, various measurements are taken as antenna 52 is moved over, and within the vicinity of, IMD 16. Correlations are then drawn between one or more recharge coupling efficiency measurements and one or more telemetry signal strength measurements.

As may be appreciated by the above discussion, for a given model of recharging unit 48, it may be desirable to develop a different signal strength map for each type of IMD that will be recharged by that recharging unit. Each signal strength map may then be stored as one of signal strength maps 83 within storage device(s) 82. If patient-specific signal strength maps are developed post-implant, a different map may be stored within storage device(s) 82 for each patient that will use recharging unit 48.

The foregoing discussion describes a signal strength map as being a table, with each entry in the table corresponding to a different data set of one or more telemetry signal strength measurements and the one or more corresponding recharge coupling efficiency measurements. If desired, a signal strength map may be embodied as one or more other types of data structures.

In yet another embodiment, a signal strength map may be represented graphically using x, y, and z coordinates. In this type of representation, each data set is associated with a unique set of x, y, and z coordinates that describe a position of the antenna relative to the IMD. Accurate repositioning of an antenna at a given location, as described by the x, y, and z coordinates, may be performed using automated mechanisms (e.g., a robotic arm) or using a manual mechanism such as a positioning grid. In this embodiment, a first "pass" may be conducted during which telemetry signal strength measurements are collected and stored for each point on the graph, as described by a unique set of x, y, and z coordinates. Sometime before or after these measurements are obtained, a second "pass" is conducted during which the recharge coupling efficiency measurements are collected for each set of x, y, and z coordinates. Alternatively, both the telemetry signal strength measurements and the recharge coupling efficiency measurements may be collected during a single "pass" for each of the x, y, and z coordinates.

Many other ways of representing and storing the measurements will be apparent to those skilled in the art. It will be appreciated that the manner of recording the data is largely unimportant, so long as the mechanism allows a given telemetry signal strength value to be readily correlated to an associated recharge coupling efficiency value.

After multiple data sets are obtained to populate a signal strength map in the above-described manner, one or more pre-processing activities may optionally be performed on those data sets before the signal strength map is put into use. Such pre-processing activities may be performed, for instance, by a microprocessor that is included as part of control circuit 80. Such a microprocessor may operate under the control of software or hardware programs 84 loaded within storage device(s) 82, for example.

Figure 11:
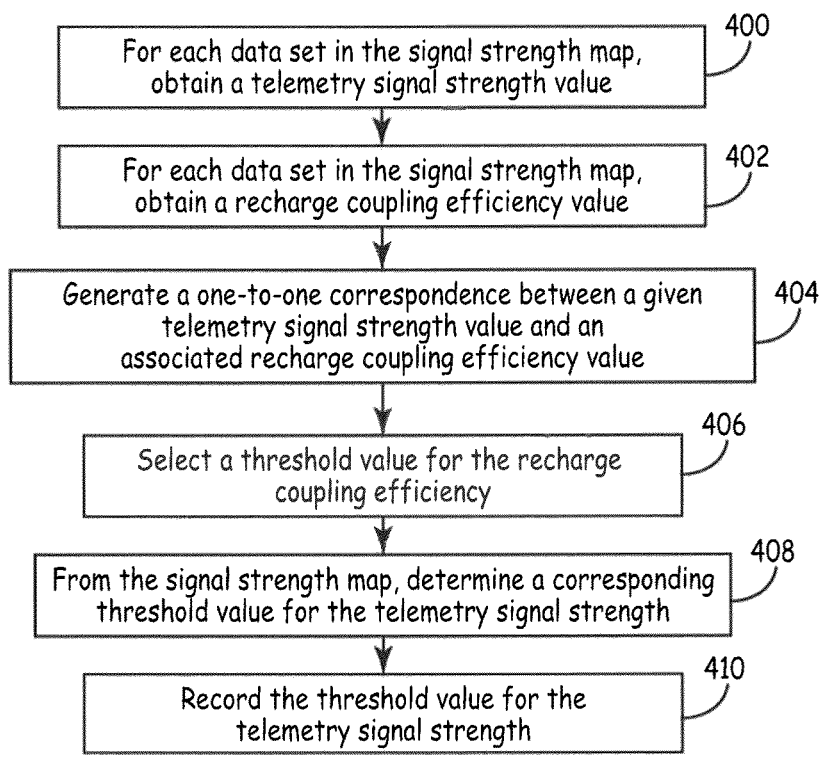
FIG. 11 is a flow diagram of one method of processing the metrics that have been obtained for use in generating a signal strength map.

FIG. 11 is a flow diagram of one method of processing the various measurements that have been gathered for use in generating a signal strength map. According to the method, for each data set (e.g., each table entry) in the map, a "primary" value may be established to represent the telemetry signal strength (400). This primary value is that which will be used to determine whether antenna positioning is adequate to establish a recharge session in the manner described in regards to FIGS. 6-8 above.

The primary signal strength value may be obtained in several ways. If only a single signal strength measurement was collected during step 362 of FIG. 10 such as one RSSI measurement obtained from receive circuit 86, no processing need be performed. That single measurement will simply be used to represent signal strength. However, if multiple measurements were collected, some processing may be desired. For instance, this may involve averaging a RSSI measurement from receive circuit 86 with a second RSSI measurement from telemetry circuit 47 of IMD 16. If desired, this average may be a weighted average. Alternatively, one of the multiple measurements may simply be selected for use as the telemetry signal strength value, with the other measurement being disregarded.

In another embodiment, processing may involve some type of normalization. For instance, a RSSI measurement from one vendor that ranges between values of 1 and 100 may be normalized to a range extending between 1 and 256, for example. Similarly, a signal strength metric that is inversely proportional to signal strength (as will be the case when an amplifier gain setting is used as a signal strength metric) may be normalized, if desired, so that a direct proportionality is established between the obtained telemetry signal strength value and recharge coupling efficiency.

The types of processing that are performed may depend on the IMD/recharger pair. For instance, for some IMDs, it may be known that a RSSI measurement obtained by the telemetry circuit of the IMD will not be as reliable as that obtained by the recharger. In that instance, a primary value for signal strength may be obtained by weighting the RSSI measurement of the recharger more heavily than that obtained from the IMD to obtain a weighted average. Alternatively, a RSSI measurement obtained from the IMD may be discounted entirely. In this manner, processing activities may be tailored to the IMD/recharger pair to create a signal strength map that is as accurate as possible for that pair.

Next, a similar step may optionally be performed to obtain a recharge coupling efficiency value for each data set (402). That is, for each data set, a single recharging coupling efficiency value may be established from the one or more measurements for recharge coupling efficiency that were gathered and stored within the entry. If only one measurement was taken for this purpose, this measurement may simply be established as the recharge coupling efficiency value. For example, assume that the only measurement taken that is indicative of recharge coupling efficiency is a measure of the current in secondary coil 34. This current measurement may be designated as the recharge coupling efficiency value, which will be expressed in a unit such as milliamps (mA).

As another example, assume that current and voltage measurements were taken for both the primary coil 54 and secondary coil 34. In this case, the percentage of power transferred from primary coil 54 to secondary coil 34 may be used to generate the recharge coupling efficiency value. This value may be calculated by determining the power associated with each of the primary coil 54 and the secondary coil 34, and then dividing the latter by the former. The result may be expressed as a percentage, as exemplified by column 152 of FIG. 5.

Other types of calculations or processing may be performed if a different metric is selected for use as the recharge coupling efficiency value. The processing is performed for each data set (i.e., each table entry).

Upon completion of processing steps 400 and 402, the various measurements obtained for telemetry signal strength and recharge coupling efficiency will have been used to derive a primary telemetry signal strength value and a corresponding recharge coupling efficiency value that may be employed during positioning of an antenna in the above-described manner. Such values are exemplified by columns 150 and 152, respectively, of FIG. 5. The various measurements that were used to derive these values may be retained within the data set, if desired (e.g., in additional table columns), although such additional measurements are not shown in FIG. 5 for ease of reference. For example, the table of FIG. 5 may contain additional table columns that store RSSI measurements used to derive the telemetry signal strength value of column 150. Other table columns may store current and voltage measurements used to derive the recharge coupling efficiency values of column 152.

Next, some processing may be required to generate a one-to-one correspondence between a given signal strength value and a recharge coupling efficiency value, as indicated by step 404. That is, after the telemetry signal strength values and the associated recharge coupling efficiency values are obtained according to steps 400 and 402 discussed above, it is possible that multiple entries may exist within the signal strength map that have a same value for the telemetry signal strength but which differ in the corresponding recharge coupling efficiency values or vice versa.

The foregoing can best be considered by returning to the example signal strength map of FIG. 5. Assume that after steps 400 and 402 of the method of FIG. 11 have been completed, the values shown in columns 150 and 152 have been established for telemetry signal strength and recoupling efficiency, respectively, with the exception that two entries exist within this signal strength map having a telemetry signal strength metric of "31". For one of these entries, the corresponding value for recharge coupling efficiency is "10%". For the other entry, the value for the recharge coupling efficiency is "11%". This type of situation may occur because there is not perfect symmetry between the electromagnetic field that couples telemetry coils 46 and 44 and the field that is setup between recharge coils 54 and 34. In this case, it may be desirable to reconcile the situation so that only a single entry is associated with this telemetry signal strength value of "31". For instance, the recharge coupling efficiency values may be averaged. In this case, a single entry having a telemetry signal strength value of "31" and a recharge coupling efficiency value of "10.5%" may be created. In another embodiment, a median value may be used for the recharge coupling efficiency instead of the average. Many other types of processing methods may be used to reconcile recharge coupling efficiency values.

It may be noted that in an embodiment wherein the recharge coil 34 and telemetry coil 4 of IMD 16 each have a regular shape (e.g., one is circular and the other is a square) and are co-axial with one another, and the recharge coil 54 and telemetry coil 36 of recharging unit 48 are likewise co-axial with one another and have a regular shape, the variations between recharge coupling efficiency values for a given telemetry signal strength value may be minimized. In this type of embodiment, use of an average or median value for recharge coupling efficiency is an acceptable approach to generating a one-to-one correspondence between telemetry signal strength values and recharge coupling efficiency values.

In some scenarios wherein coils of recharging unit 48 are not co-axial with one another, the coils of IMD 16 are not co-axial with one another, the coils of recharging unit are not co-axial with the coils of IMD, or one or more of coils 34, 44, 46 or 54 are of an irregular shape, telemetry field strength may be very asymmetrical with respective to recharging field strength. In this case, use of the current mechanisms may not be possible. For instance, if the variations between recharging coupling efficiency values for a given telemetry signal strength value vary by more than a predetermined percentage (e.g., more than 5%, as when one recharge coupling efficiency value is 10% and another recharge coupling efficiency value is 16%), it may be determined that the current techniques are not applicable to the IMD/recharger device pair.

Step 404 may optionally include a process of ordering the data sets. For instance, it may be desirable to order data sets within a signal strength map so that the data sets are arranged with telemetry signal strength values appearing in ascending or descending order. This may aid in searching the signal strength map for a particular telemetry signal strength value.

Returning to FIG. 11, after a reliable correspondence is generated between a given telemetry signal strength value and the recharge coupling efficiency value in step 404, a threshold may be selected for recharge coupling efficiency (406). For instance, assume that the signal strength map of FIG. 5 has been developed. A qualified clinician may next determine that for a recharge session to be effective, power transfer between the primary and secondary coils must reach an efficiency of at least 75%, which is therefore established as the recharge coupling efficiency threshold value.

As discussed above, it is possible (albeit unintuitive) to derive a signal strength map that utilizes a recharge coupling efficiency value which is inversely proportional to the actual recharge coupling efficiency. The recharge coupling efficiency threshold value in this instance will be a maximum, rather than a minimum, value.

In one embodiment, a threshold value for recharge coupling efficiency may be programmably selected. For instance, the threshold may be selected based on a make/model for the IMD/recharger device pair. In this case, a particular recharge coupling efficiency threshold may be obtained from a look-up table based on the IMD/recharger pair. In another embodiment, the recharging coupling efficiency threshold value may be selected by a clinician or technician to be specific to a particular instance of an IMD/recharging unit device pair and/or to a particular patient. Alternatively, the threshold may be a fixed number that is the same regardless of the devices being used. In another embodiment, a user may select the threshold value for a given recharge session prior to initiating that session.

After the recharge coupling efficiency threshold value has been selected, an entry within the signal strength map is located that contains, or most closely approximates, the recharge coupling efficiency threshold value. The corresponding value for the telemetry signal strength may then be designated as the telemetry signal strength threshold value (408). This telemetry signal strength threshold value may then be recorded in conjunction with the telemetry signal strength map (410). This telemetry signal strength threshold value may be used when attempting to position antenna 52 in the manner discussed above. In particular, it may be determined that an adequate recharge session cannot be established until the telemetry signal strength threshold value is obtained. As discussed above, if a direct correspondence exists between the telemetry signal strength metric and recharge coupling efficiency, this will involve repositioning the antenna until a telemetry signal strength value is obtained that is at least the telemetry signal strength threshold value. Otherwise, this will involve continuing antenna repositioning until a telemetry signal strength value is obtained that is at most the telemetry signal strength threshold value.

As discussed above, a different signal strength map may be generated based on the type of the IMD and the type of the recharging unit. Alternatively, a different map may be created for a specific instance of an IMD and recharging unit (e.g., based on the serial numbers of those devices). The latter embodiment takes into account tolerances in the circuitry of the IMD and recharging unit, as well as specifics concerning the particular implant scenario, assuming the signal strength map is generated post-implant.

After a signal strength map has been created in the aforementioned manner, it may be stored as one of signal strength map(s) 83 within storage devices 82 of recharging unit 48. Alternatively or additionally, a signal strength map that is specific to a particular device may be stored as one of signal strength map(s) 53 within storage device(s) 51.

The above discussion focuses on developing a signal strength map using an empirical approach. That is, measurements are taken, and optional processing activities may be utilized, to develop a correlation between recharge coupling efficiency and telemetry signal strength as a position of an antenna is varied in relation to the position of an IMD. Another method may instead use modeling to generate a particular signal strength map. That is, mathematical relationships governing electromagnetic field signal strengths can be used to develop a model for a given IMD 16 and a particular recharging unit 48. Such a model will take into account the physical, electrical, and magnetic characteristics of the devices, including the shape, size, physical structure, orientation, etc. of the telemetry and recharge coils of the device pair. Such models may be used to generate data sets that include an indication of recharge coupling efficiency as well as an indication of telemetry signal strength when the antenna of the modeled recharging unit is a selected distance and orientation relative to the IMD. The data sets may then be used to populate a signal strength map corresponding to the model.

Once a signal strength map is generated using either an empirical approach or modeling techniques, that map is stored for later use. For instance, the signal strength map may be stored within a storage device of recharging unit 48, IMD 16, a clinician programmer, and/or a patient programmer. The map must then be retrieved for use when a recharge session is about to be initiated between a corresponding IMD/recharger pair. This may occur as follows.

Figure 12:
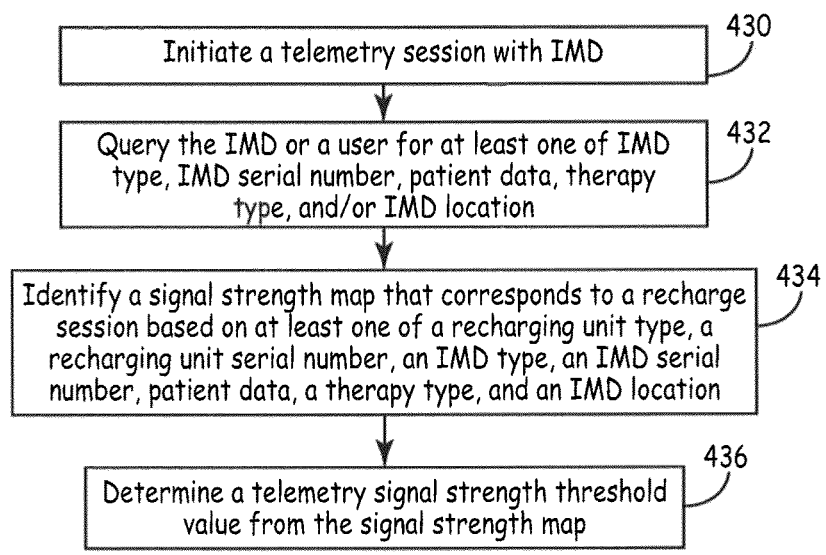
FIG. 12 is a flow diagram illustrating one method of preparing to initiate a recharging session according to the current invention.

FIG. 12 is a flow diagram illustrating one method of preparing to initiate a recharge session according to the current invention. The steps of FIG. 12 may be performed during step 182 (FIG. 6) or during step 252 (FIG. 7), for example. During the preparation process, a user may optionally position antenna 52 of recharging unit 48 in proximity to IMD 16 and initiate a telemetry session (430). Once a telemetry session has been established, a telemetry downlink transmission may then query the IMD for information concerning the IMD, including IMD type, IMD serial number, patient data, therapy type and/or IMD implant location (432). Alternatively, some or all of this information may be obtained from a user via user interface devices 94, as by a user entering information via keypad 98.

Control circuit 80 of recharging device 50 may then identify an appropriate signal strength map for use based on at least one of the type of recharging unit, the recharging unit serial number, the type of IMD, an IMD serial number, patient data, a therapy type and/or IMD location (434). Patient data may include a patient name or patient ID number, for instance. Information such as therapy type and/or IMD location may allow for selecting a signal strength map that corresponds to an appropriate IMD depth and/or orientation, as may be required if using signal strength maps developed pre-implant.

The signal strength map that is identified for use may be one of signal strength maps 83 stored within storage device(s) 82 of recharging device 50. The signal strength map may instead be retrieved from storage device(s) 51 of IMD during an uplink transmission. Alternatively, the map may be obtained from a patient or clinician programmer.

Next, a telemetry signal strength threshold value may be retrieved from the identified signal strength map (436). This is the value that must be obtained for telemetry signal strength before recharge may be initiated. Once the signal strength map and the corresponding telemetry signal strength value have been identified, positioning of antenna 52 may be initiated according to the current invention. Exemplary methods of accomplishing this are discussed in reference to FIGS. 6 and 7 above.

The above-described embodiments discuss signal strength maps that are static. That is, once the signal strength map is created and ready for use, it is not updated. In another embodiment, signal strength maps may be dynamically adapted to a particular patient and IMD/recharging unit pair. According to this approach, a signal strength map that was developed pre-implant, and which need not be specific to a given patient or a given instance of a IMD/recharging unit pair, is available for use during a first recharge session of an IMD following implant. During this first recharge session, and/or during one or more subsequent recharge sessions, data is collected to update the data sets contained within the signal strength map. In this way, the signal strength map becomes increasingly more tailored to a particular patient over time. If desired, data collection may occur each time the signal strength map is used, during each of the first N sessions of use, or at selected periodic increments (e.g., during each fourth use). In another embodiment, the user is allowed to select whether a current recharge session is to include data collection.

Figure 13:
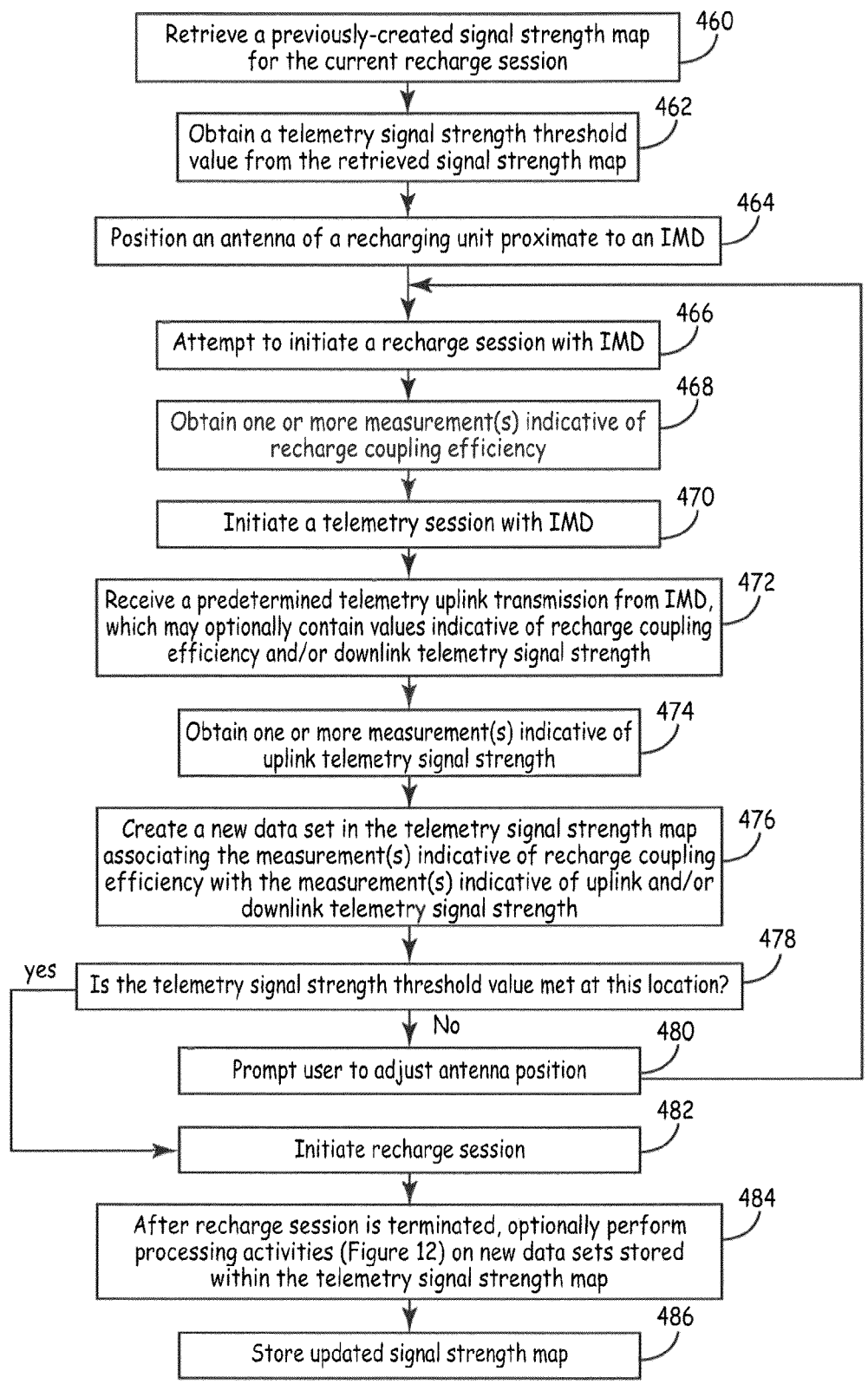
FIG. 13 is a flow diagram illustrating one method of adaptively updating a signal strength map during use.

FIG. 13 is a flow diagram illustrating one method of adaptively updating a signal strength map during use. In preparation to initiate a current recharge session, a previously-created signal strength map is obtained for use with the particular IMD/recharging unit device pair (460). This signal strength map may have been created pre-implant, for example.

Next, a telemetry signal strength threshold value may be retrieved from this signal strength map (462). As discussed above, this is the telemetry signal strength value that must be obtained between recharging unit 48 and IMD 16 before a recharge session will be initiated.

Antenna 52 of recharging unit 48 is then positioned at a predetermined point relative to an IMD (464). An attempt is made to initiate a recharge session with the IMD (466). During this attempt, one or more measurement(s) indicative of recharge coupling efficiency are obtained (468). Such measurement(s) may include one or more of a measure of a current in primary coil 54, a voltage across primary coil, the loading on the primary coil, a current in secondary coil 34, and/or voltage across the secondary coil.

A telemetry session may then be established with IMD 16 (470). This may prompt IMD 16 to return an uplink telemetry transmission to recharging unit 48 (472). This uplink transmission may optionally include one or more measurements that were taken by IMD 16 to describe recharge efficiency. This transmission may further include a measurement obtained by the IMD that describes downlink telemetry signal strength. The signal strength of this uplink telemetry transmission may be measured (474). A new data set may be created within the signal strength map that associates the one or more measurements indicative of recharge coupling efficiency with the one or more measurements indicative of uplink and/or downlink telemetry signal strength (476).

It may next be determined whether the telemetry signal strength threshold value has been met at this location (478). This may involve performing some type of processing on the one or more telemetry signal strength measurements. For instance, an average may be obtained for the uplink and downlink telemetry signal strength measurements, and the average is used to determine whether the threshold has been met. If the threshold has not been met, the user is prompted to adjust the position of the antenna (480). Processing then returns to step 466 where another attempt is made to initiate a recharge session with the IMD 16.

If the threshold for telemetry signal strength has been met in step 480, the recharge session may be re-initiated (482). This may occur automatically, or the user may be prompted to perform some action to initiate the session. This recharge session may then continue for a predetermined period of time, until the user terminates the session, or upon the occurrence of some other terminating event.

After the recharge session is terminated, some processing activities may optionally be performed on the newly acquired data sets stored within the telemetry signal strength map (484). Such processing activities may occur to place the data in a same format as the previously-stored data sets of the signal strength map, and to remove duplicate entries. This processing may occur according to the steps of FIG. 12, for instance. Any updates associated with the processing activities may be stored in the signal strength map, which may be retained as one of signal strength maps 83 within storage device(s) 82 of recharging device 50, as one of signal strength maps 53 within storage device(s) 51 of IMD 16, in a storage device of a programming unit, or in some other retentive storage.

It will be appreciated that FIG. 13 is exemplary only and other embodiments exist. For instance, FIG. 13 may include steps that provide informational feedback to a patient in a manner similar to that shown in steps 306 and 310 of FIG. 8. Moreover, the ordering of the steps of FIG. 13 is, in many cases, unimportant. Many of the steps may be performed in a different order without impacting the spirit of the invention. If desired, the recharge session of step 482 may be periodically suspended so that another set of measurements may be taken and stored within signal strength map. In this manner, additional data sets may be created that take into account any small movements of the antenna that occur during recharge.

The method of FIG. 13 provides a mechanism to adapt a pre-existing recharge map to a particular user and IMD/recharging unit device pair. This will take into account any changes that occur in the circuitry of the IMD or the recharging unit over time, changes that occur in the patient's body (e.g., loss/gain of fat or muscle mass and/or device orientation), any alterations associated with addition or removal of other IMDs within the patient's body, and so on.

Because the process of FIG. 13 may take longer than the non-adaptive methods of FIGS. 6-7, it may be desirable to allow a patient to select when the adaptive approach will be activated. For instance, the user may employ a menu provided on display screen 96 to select this approach when he or she has more time to spend recharging the device.

In one embodiment, configuration parameters may be programmed to select use of the adaptive approach during a first predetermined number of recharge sessions for a device (e.g., during the first ten recharge sessions following implant), during a predetermined time period of use (e.g., the first month following implant), at periodic increments (every fifth recharge session or the first week of every month), and/or at some other selectable periodic increment.

FIG. 13 updates a signal strength map while the signal strength map is in use in preparation to initiate a recharge session. The signal strength map may likewise be adapted over time utilizing processes similar to those shown in FIGS. 10 and 11 that are performed solely to update the signal strength map and without the initiation of a recharge session. For instance, such a procedure may be initiated by a clinician when a patient is undergoing a routine health screening.

The above-described embodiments provide efficient mechanisms for initiating recharge sessions between a recharging unit and an IMD. The described systems and methods will be understood to be merely exemplary. For instance, those skilled in the art will appreciate that the steps of the various flow diagrams may, in many cases, be re-ordered without impacting the spirit of the invention. Some steps of these processes are optional and may be omitted entirely. These processes may be implemented by programmed instructions such as software and/or firmware instructions that are stored within storage devices 82 of recharging device 50 and/or storage devices 51 of IMD 16. The processes may instead be implemented in hardware, or some combination of hardware and programmed instructions.

In addition to the foregoing, the system block diagrams are illustrative only, and many other types of system configurations may be utilized within the scope of the current invention. Additionally, many types of IMDs may usefully employ the current invention. For instance, although FIG. 3 illustrates an IMD implanted close to cutaneous boundary 38, the current invention may be readily employed with an IMD implanted deeper within the patient's body. Thus, the description is to be considered illustrative only, with the scope of the invention to be determined by the Claims that follow.

What is claimed is:

1. A method for utilizing a recharging unit to recharge a rechargeable power source of an Implantable Medical Device (IMD), comprising:
    transmitting at least one telemetry signal between the recharging unit and the IMD;
    determining, by a communication circuit, an indication of signal strength of the at least one telemetry signal; and based on the indication of signal strength, determining, by a control circuit, whether adequate determining whether adequate recharge coupling efficiency exists to initiate a recharge session;

wherein transmitting at least one telemetry signal between the recharging unit and the IMD comprises receiving at least one telemetry signal by the recharging unit and wherein determining an indication of signal strength of the at least one telemetry signal comprises determining a signal strength of the at least one telemetry signal received by the recharging unit.

2. The method of claim 1, further including using the indication of signal strength to determine a corresponding recharge coupling efficiency value of the recharge session that may be initiated.

3. The method of claim 2, further including providing at least one of the indication of signal strength and the recharge coupling efficiency value to a user.

4. The method of claim 1, further including providing an indication to a user that an antenna of the recharging unit must be repositioned relative to the IMD.

5. The method of claim 1, further including automatically initiating the recharge session based on determining adequate recharge coupling efficiency exists.

6. The method of claim 5, further including:
after the recharge session is initiated, transmitting at least one telemetry signal between the recharging unit and the IMD;
determining an indication of signal strength of the at least one telemetry signal that was transmitted after the recharge session was initiated; and based thereupon,
providing an indication to a user as to whether an antenna of the recharging unit must be repositioned relative to the IMD.

7. The method of claim 1, further including determining whether the indication of signal strength has a predetermined relationship to a signal strength threshold value, and if so, indicating that the recharge session may be initiated.

8. The method of claim 7, further including retrieving at least one of the signal strength threshold value and the predetermined relationship from a signal strength map.

9. The method of claim 8, further including selecting the signal strength map that is to be used based on at least one of a group consisting of a type of the IMD, serial number of the IMD, a type of the recharging unit, serial number of the recharging unit, data describing a patient, a therapy type being provided by the IMD, and a location of the IMD.

10. The method of claim 1, further including providing a signal strength map that provides associations between indications of recharge coupling efficiency and indications of signal strength for telemetry signals, and wherein the determination as to whether the recharge session may be initiated is based on the associations provided by the signal strength map.

11. The method of claim 10, further including generating an association to be included in the signal strength map, the association generated by:
positioning an antenna of the recharging unit at a location relative to the IMD;
transmitting a telemetry signal between the antenna and the IMD;
obtaining an indication of signal strength for the transmitted telemetry signal;
obtaining an indication of recharge coupling efficiency between the antenna and the IMD; and
generating an association between the obtained indication of signal strength and the obtained indication of recharge coupling efficiency.

12. The method of claim 10, wherein at least some of the associations are generated adaptively over time.

13. The method of claim 10, wherein at least some of the associations are generated while the signal strength map is being used to determine whether to initiate the recharge session.

14. The method of claim 10, wherein at least some of the associations are generated after the IMD is implanted in a body.

15. The method of claim 1, further comprising:
determining a threshold value for the recharge coupling efficiency;
identifying a signal strength threshold value based on the threshold value for the recharge coupling efficiency; and
comparing the signal strength threshold value to the indication of signal strength of the at least one telemetry signal to determine whether the recharge session may be initiated.

16. For use by a recharging unit that is adapted to recharge a power source of an Implantable Medical Devices (IMD), a storage device configured to store programmed instructions to cause a control circuit of the recharging unit to perform a method, comprising:
transmitting a telemetry signal between the IMD and the recharging unit;
obtaining an indication of signal strength of the telemetry signal; and
determining, based the indication of signal strength, whether to initiate a recharge session between the recharging unit and the IMD;
wherein transmitting at telemetry signal between the IMD and the recharging unit comprises receiving a telemetry signal by the recharging unit and wherein obtaining the indication of signal strength comprises obtaining a signal strength of the telemetry signal received by the recharging unit.

17. The storage device of claim 16, wherein the method further comprises:
determining, from the indication of signal strength, a recharge coupling efficiency that may be achieved between the IMD and the recharging unit; and
determining based on at least one of the indication of signal strength and the recharge coupling efficiency whether to initiate the recharge session.

18. The storage device of claim 16, wherein the method further comprises using a signal strength map that associates indications of signal strength to recharge coupling efficiency to determine whether to initiate the recharge session.

19. The storage device of claim 18, wherein the method further comprises updating the signal strength map to include an association between the indication of signal strength for the telemetry signal and recharge coupling efficiency that would exist during a recharge session between the IMD and the recharging unit.

20. The storage device of claim 19, wherein updating the signal strength map occurs while positioning an antenna of the recharging unit prior to initiating the recharge session.

21. The storage device of claim 16, wherein the method further comprises performing one of initiating the recharge session and providing an indication to reposition an antenna of the recharging unit based on determining whether to initiate the recharge session.

22. A system, comprising:
   a coil of a recharging unit configured to receive a telemetry signal from an Implantable Medical Device (IMD);
   a communication circuit configured to provide an indication of a strength of the telemetry signal received by the coil; and
   a control circuit configured to determine, based on the indication of signal strength, whether recharge coupling efficiency is adequate to initiate a recharge session between the recharging unit and the IMD.

23. The system of claim 22, wherein the control circuit is configured to determine a recharge coupling efficiency value corresponding to the indication of signal strength.

24. The system of claim 22, further including a user interface device configured to communicate the indication of signal strength to a user.

25. The system of claim 22, wherein the communication circuit is configured to determine the indication of signal strength based on strength of a telemetry signal transmitted by the coil to the IMD.

26. The system of claim 22, further including a storage device configured to store at least one signal strength map that associates each of one or more indications of signal strength with a respective recharge coupling efficiency value.

27. The system of claim 26, wherein the control circuit is configured to update the signal strength map.

28. The system of claim 22, wherein the control circuit is adapted to automatically initiate a recharge session with the IMD if it is determined recharge coupling efficiency is adequate.

29. A system, comprising:
   an external coil configured to exchange a telemetry signal with an internal coil of an Implantable Medical Device (IMD);
   a communication circuit configured to provide an indication of signal strength of the exchanged telemetry signal; and
   a control circuit configured to determine based on the indication of signal strength whether recharge coupling efficiency is adequate.

30. The system of claim 29, wherein the exchanged telemetry signal is transmitted from the internal telemetry coil and received by the external coil.

31. The system of claim 30, further comprising the IMD.

32. The system of claim 30, further comprising a primary recharge coil configured to inductively couple to a secondary recharge coil of the IMD to recharge a rechargeable power source of the IMD.

33. The system of claim 32, further including a user interface device configured to provide a user with an indication to reposition the primary recharge coil that is based on the indication of signal strength.

34. The system of claim 30, wherein the external coil is configured to exchange with the internal coil of the IMD a telemetry signal that is transmitted after a recharge session has been initiated.

35. The system of claim 34, wherein the control circuit is configured to provide an indication of whether recharge coupling efficiency of the recharge session that has been initiated is adequate based on the telemetry signal that was transmitted after a recharge session was initiated.

36. The system of claim 30, wherein the control circuit is adapted to automatically initiate a recharge session with the IMD if it is determined recharge coupling efficiency is adequate.

37. The system of claim 29, wherein the communication circuit is configured to determine the indication of signal strength based on a downlink telemetry transmission transmitted to the IMD.

* * * * *

UNITED STATES PATENT AND TRADEMARK OFFICE
CERTIFICATE OF CORRECTION

PATENT NO.        : 8,509,909 B2           Page 1 of 1
APPLICATION NO.   : 12/100875
DATED             : August 13, 2013
INVENTOR(S)       : Figueiredo et al.

It is certified that error appears in the above-identified patent and that said Letters Patent is hereby corrected as shown below:

In the Claims

Claim 1, Col. 31, Line 2: "whether adequate" should read --whether adequate recharge coupling efficiency--

Signed and Sealed this
Third Day of June, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,509,909 B2  
APPLICATION NO.   : 12/100875  
DATED             : August 13, 2013  
INVENTOR(S)       : Figueiredo et al.

Page 1 of 1

It is certified that error appears in the above-identified patent and that said Letters Patent is hereby corrected as shown below:

In the Claims

Claim 1, Col. 31, Line 2: "whether adequate determining whether" should read --whether--

This certificate supersedes the Certificate of Correction issued June 3, 2014.

Signed and Sealed this  
Thirteenth Day of January, 2015

Michelle K. Lee  
*Deputy Director of the United States Patent and Trademark Office*